(12) United States Patent
Gilbert et al.

(10) Patent No.: US 7,603,897 B2
(45) Date of Patent: Oct. 20, 2009

(54) DOWNHOLE PROBE ASSEMBLY

(75) Inventors: Gregory N. Gilbert, Sugar Land, TX (US); Mark A. Sitka, Richmond, TX (US); Malcolm Douglas McGregor, The Woodlands, TX (US); Glenn C. Gray, Austin, TX (US); John R. Hardin, Jr., Spring, TX (US); Christopher Anthony Maranuk, Houston, TX (US); James E. Stone, Porter, TX (US); Kristopher V. Sherrill, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 309 days.

(21) Appl. No.: 11/133,643

(22) Filed: May 20, 2005

(65) Prior Publication Data

US 2005/0257629 A1 Nov. 24, 2005

Related U.S. Application Data

(60) Provisional application No. 60/573,294, filed on May 21, 2004.

(51) Int. Cl.
*E21B 49/00* (2006.01)
(52) U.S. Cl. .................................................. 73/152.25
(58) Field of Classification Search .............. 73/152.24, 73/152.25, 152.26
See application file for complete search history.

(56) References Cited

U.S. PATENT DOCUMENTS

| 3,173,485 A | 3/1965 | Bretzke, Jr. |
| 3,338,307 A | 8/1967 | Redwine |
| 3,356,137 A | 12/1967 | Raugust |

(Continued)

FOREIGN PATENT DOCUMENTS

EP 0697501 A2 2/1996

(Continued)

OTHER PUBLICATIONS

Joel L. Hebert; "A Method for Planning and Performing a Pressure Survey to Achieve Desired Accuracy of Pressure Gradient"; 2002 ASME Engineering Technology Conference on Energy; Feb. 4-5, 2002; pp. 1-8; ETCE 2002; American Society of Mechanical Engineers; Houston, Texas, U.S.A.

(Continued)

*Primary Examiner*—Robert R Raevis
(74) *Attorney, Agent, or Firm*—Conley Rose, P.C.

(57) ABSTRACT

A downhole, extendable apparatus and methods of use are described and claimed herein. In one embodiment, the extendable apparatus includes a piston that extends toward a borehole wall, the piston having an inner sampling member that is also extendable. The sampling member may be further extended to engage the borehole wall and penetrate the formation. The sampling member may also include a screen and an inner scraper or wiper that frictionally engages the screen and reciprocates to remove debris from the screen. The piston may comprise a seal pad having an internal cavity for receiving a volume of fluid. In another embodiment, the extendable apparatus comprises multiple, concentric pistons for extending the sampling member further toward the borehole wall than is possible with a single piston. The extendable apparatus may also include a retraction contact switch and position indicator.

26 Claims, 19 Drawing Sheets

U.S. PATENT DOCUMENTS

| | | | |
|---|---|---|---|
| 3,530,933 A | 9/1970 | Whitten | |
| 3,565,169 A | 2/1971 | Bell | |
| 3,811,321 A | 5/1974 | Urbanosky | |
| 3,813,936 A | 6/1974 | Urbanosky et al. | |
| 3,858,445 A | 1/1975 | Urbanosky | |
| 3,859,850 A | 1/1975 | Whitten et al. | |
| 3,859,851 A | 1/1975 | Urbanosky | |
| 3,864,970 A | 2/1975 | Bell | |
| 3,924,463 A | 12/1975 | Urbanosky | |
| 3,934,468 A * | 1/1976 | Brieger | 73/152.25 |
| 3,952,588 A | 4/1976 | Whitten | |
| 4,210,018 A | 7/1980 | Brieger | |
| 4,246,782 A | 1/1981 | Hallmark | |
| 4,248,081 A | 2/1981 | Hallmark | |
| 4,270,385 A | 6/1981 | Hallmark | |
| 4,282,750 A | 8/1981 | Prats et al. | |
| 4,287,946 A | 9/1981 | Brieger | |
| 4,292,842 A | 10/1981 | Hallmark | |
| 4,339,948 A | 7/1982 | Hallmark | |
| 4,375,164 A | 3/1983 | Dodge et al. | |
| 4,416,152 A | 11/1983 | Wilson | |
| 4,434,653 A | 3/1984 | Montgomery | |
| 4,507,957 A | 4/1985 | Montgomery et al. | |
| 4,513,612 A | 4/1985 | Shalek | |
| 4,593,560 A | 6/1986 | Purfurst | |
| 4,671,322 A | 6/1987 | Purfurst | |
| 4,712,613 A | 12/1987 | Nieuwstad | |
| 4,720,996 A | 1/1988 | Marsden et al. | |
| 4,742,459 A | 5/1988 | Lasseter | |
| 4,745,802 A * | 5/1988 | Purfurst | 73/152.26 |
| 4,782,695 A | 11/1988 | Glotin et al. | |
| 4,833,914 A | 5/1989 | Rasmus | |
| 4,843,878 A | 7/1989 | Purfurst et al. | |
| 4,845,982 A | 7/1989 | Gilbert | |
| 4,860,580 A | 8/1989 | DuRocher | |
| 4,860,581 A | 8/1989 | Zimmerman et al. | |
| 4,862,967 A | 9/1989 | Harris | |
| 4,879,900 A | 11/1989 | Gilbert | |
| 4,884,439 A | 12/1989 | Baird | |
| 4,890,487 A | 1/1990 | Dussan V. et al. | |
| 4,893,505 A | 1/1990 | Marsden et al. | |
| 4,936,139 A | 6/1990 | Zimmerman et al. | |
| 4,941,350 A | 7/1990 | Schneider | |
| 4,949,575 A | 8/1990 | Rasmus | |
| 4,951,749 A * | 8/1990 | Carroll | 166/264 |
| 4,962,665 A | 10/1990 | Savage et al. | |
| 4,994,671 A | 2/1991 | Safinya et al. | |
| 5,056,595 A | 10/1991 | Desbrandes | |
| 5,095,745 A | 3/1992 | Desbrandes | |
| 5,148,705 A | 9/1992 | Desbrandes | |
| 5,166,747 A | 11/1992 | Schroeder et al. | |
| 5,167,149 A | 12/1992 | Mullins et al. | |
| 5,184,508 A | 2/1993 | Desbrandes | |
| 5,201,220 A | 4/1993 | Mullins et al. | |
| 5,207,104 A | 5/1993 | Enderlin | |
| 5,230,244 A | 7/1993 | Gilbert | |
| 5,233,866 A | 8/1993 | Desbrandes | |
| 5,247,830 A | 9/1993 | Goode | |
| 5,265,015 A | 11/1993 | Auzerais et al. | |
| 5,269,180 A | 12/1993 | Dave et al. | |
| 5,279,153 A | 1/1994 | Dussan V. et al. | |
| 5,303,582 A | 4/1994 | Miska | |
| 5,303,775 A | 4/1994 | Michaels et al. | |
| 5,329,811 A | 7/1994 | Schultz et al. | |
| 5,335,542 A | 8/1994 | Ramakrishnan et al. | |
| 5,353,637 A | 10/1994 | Plumb et al. | |
| 5,377,755 A | 1/1995 | Michaels et al. | |
| 5,473,939 A | 12/1995 | Leder et al. | |
| 5,517,854 A | 5/1996 | Plumb et al. | |
| 5,549,159 A | 8/1996 | Shwe et al. | |
| 5,549,162 A | 8/1996 | Moody et al. | |
| 5,587,525 A | 12/1996 | Shwe et al. | |
| 5,602,334 A | 2/1997 | Proett et al. | |
| 5,622,223 A | 4/1997 | Vasquez | |
| 5,635,631 A | 6/1997 | Yesudas et al. | |
| 5,644,076 A | 7/1997 | Proett et al. | |
| 5,663,559 A | 9/1997 | Auzerais et al. | |
| 5,672,819 A | 9/1997 | Chin et al. | |
| 5,703,286 A | 12/1997 | Proett et al. | |
| 5,708,204 A | 1/1998 | Kasap | |
| 5,741,962 A | 4/1998 | Birchak et al. | |
| 5,770,798 A | 6/1998 | Georgi et al. | |
| 5,789,669 A | 8/1998 | Flaum | |
| 5,803,186 A | 9/1998 | Berger et al. | |
| 5,924,499 A | 7/1999 | Birchak et al. | |
| 5,934,374 A | 8/1999 | Hrametz et al. | |
| 5,969,241 A | 10/1999 | Auzerais | |
| 6,026,915 A | 2/2000 | Smith et al. | |
| 6,044,325 A | 3/2000 | Chakravarthy et al. | |
| 6,047,239 A | 4/2000 | Berger et al. | |
| 6,058,773 A | 5/2000 | Zimmerman et al. | |
| 6,092,416 A | 7/2000 | Halford et al. | |
| 6,109,370 A | 8/2000 | Gray | |
| 6,111,409 A | 8/2000 | Edwards et al. | |
| 6,128,949 A | 10/2000 | Kleinberg | |
| 6,157,893 A | 12/2000 | Berger et al. | |
| 6,164,126 A | 12/2000 | Ciglenec et al. | |
| 6,178,815 B1 | 1/2001 | Felling et al. | |
| 6,223,822 B1 | 5/2001 | Jones | |
| 6,230,557 B1 | 5/2001 | Ciglenec et al. | |
| 6,247,542 B1 | 6/2001 | Kruspe et al. | |
| 6,274,865 B1 | 8/2001 | Schroer et al. | |
| 6,301,959 B1 * | 10/2001 | Hrametz et al. | 73/152.23 |
| 6,334,489 B1 | 1/2002 | Shwe et al. | |
| 6,343,507 B1 | 2/2002 | Felling et al. | |
| 6,350,986 B1 | 2/2002 | Mullins et al. | |
| 6,388,251 B1 | 5/2002 | Papanyan | |
| 6,415,648 B1 | 7/2002 | Peeters | |
| 6,427,530 B1 | 8/2002 | Krueger et al. | |
| 6,439,307 B1 | 8/2002 | Reinhardt | |
| 6,446,736 B1 | 9/2002 | Kruspe et al. | |
| 6,474,152 B1 | 11/2002 | Mullins et al. | |
| 6,476,384 B1 | 11/2002 | Mullins et al. | |
| 6,478,096 B1 | 11/2002 | Jones et al. | |
| 6,513,606 B1 | 2/2003 | Krueger | |
| 6,516,898 B1 | 2/2003 | Krueger | |
| 6,568,487 B2 | 5/2003 | Meister et al. | |
| RE38,129 E | 6/2003 | Kleinberg | |
| 6,581,455 B1 | 6/2003 | Berger et al. | |
| 6,585,045 B2 | 7/2003 | Lee et al. | |
| 6,609,568 B2 | 8/2003 | Krueger et al. | |
| 6,637,524 B2 | 10/2003 | Kruspe et al. | |
| 6,640,908 B2 | 11/2003 | Jones et al. | |
| 6,655,458 B2 | 12/2003 | Kurkjian et al. | |
| 6,658,930 B2 | 12/2003 | Abbas | |
| 6,659,177 B2 | 12/2003 | Bolze et al. | |
| 6,668,924 B2 | 12/2003 | Bolze et al. | |
| 6,672,386 B2 | 1/2004 | Krueger et al. | |
| 6,688,390 B2 | 2/2004 | Bolze et al. | |
| 6,719,049 B2 | 4/2004 | Sherwood et al. | |
| 6,729,399 B2 | 5/2004 | Follini et al. | |
| 6,745,835 B2 | 6/2004 | Fields | |
| 2001/0035289 A1 | 11/2001 | Runia | |
| 2002/0046835 A1 | 4/2002 | Lee et al. | |
| 2002/0060094 A1 * | 5/2002 | Meister et al. | 175/50 |
| 2002/0084072 A1 | 7/2002 | Bolze et al. | |
| 2002/0112854 A1 | 8/2002 | Krueger et al. | |
| 2002/0129936 A1 | 9/2002 | Cernosek | |
| 2002/0185313 A1 | 12/2002 | Jones et al. | |
| 2002/0189338 A1 | 12/2002 | Kruspe et al. | |
| 2002/0189339 A1 | 12/2002 | Montalvo et al. | |
| 2003/0042021 A1 | 3/2003 | Bolze et al. | |
| 2003/0062472 A1 | 4/2003 | Mullins et al. | |
| 2003/0066646 A1 | 4/2003 | Shammai et al. | |

| | | | |
|---|---|---|---|
| 2003/0145652 A1* | 8/2003 | Arian | 73/152.26 |
| 2003/0146022 A1 | 8/2003 | Krueger | |
| 2003/0167834 A1 | 9/2003 | Weintraub et al. | |
| 2003/0214879 A1 | 11/2003 | Proett et al. | |
| 2003/0226663 A1 | 12/2003 | Krueger et al. | |
| 2004/0007058 A1 | 1/2004 | Rylander et al. | |
| 2004/0011525 A1 | 1/2004 | Jones et al. | |
| 2004/0020649 A1 | 2/2004 | Fields | |
| 2004/0026125 A1 | 2/2004 | Meister et al. | |
| 2004/0035199 A1 | 2/2004 | Meister et al. | |
| 2004/0045706 A1 | 3/2004 | Pop et al. | |
| 2004/0050153 A1 | 3/2004 | Krueger et al. | |
| 2004/0050588 A1 | 3/2004 | Follini et al. | |
| 2004/0099443 A1 | 5/2004 | Meister et al. | |
| 2004/0173351 A1 | 9/2004 | Fox et al. | |
| 2004/0230378 A1 | 11/2004 | Proett et al. | |
| 2004/0231408 A1 | 11/2004 | Shammai | |
| 2004/0231841 A1 | 11/2004 | Niemeyer et al. | |
| 2004/0231842 A1 | 11/2004 | Shammai et al. | |

FOREIGN PATENT DOCUMENTS

| | | |
|---|---|---|
| EP | 0994238 A2 | 4/2000 |
| EP | 0978630 A2 | 9/2002 |
| GB | 2 304 906 | 3/1997 |
| WO | WO 01/33044 A1 | 5/2001 |
| WO | WO 01/33045 A1 | 5/2001 |
| WO | WO 01/98630 A1 | 12/2001 |
| WO | WO 02/08570 A1 | 1/2002 |

OTHER PUBLICATIONS

A.H. Akram et al.; "A Model to Predict Wireline Formation Tester Sample Contamination"; 1998 SPE Annual Technical Conference and Exhibition; Sep. 27-30, 1998; pp. 27-33; SPE 48959; Society of Petroleum Engineers, Inc.; New Orleans, Louisiana, U.S.A.

R. Desbrandes, et al.; "A New Concept in Wireline Formation Testing: Extended Drawdown," 13th CWLS Formation Evaluation Symp.; 1991; Calgary, Canada; pp. 1-25.

Yi Shaoguo et al.; "A New Flow Model of Pressure Response to Wireline Formation Testing"; Journal of Jianghan Petroleum Institute; vol. 19, No. 3; Sep. 1997; pp. 42-45. (Partial translation attached).

E. Kasap; "A New, Simplified, Unified Technique For The Analysis of Wireline Formation Test Data"; SPWLA 37th Annual Logging Symposium; Jun. 16-19, 1996; pp. 1-13.

Kun Huang; "A Study of Dimensionless Parameters and Formation Rate Analysis Technique for Interpretation of WFT Data"; 1996; pp. 1-147; University of Tulsa; Tulsa, Oklahoma, U.S.A.

Mark A. Proett et al.; "Advanced Permeability and Anistropy Measurements While Testing and Sampling in Real-Time Using a Dual Probe Formation Tester"; 2000 SPE Annual Technical Conference and Exhibition; Oct. 1-4, 2000; pp. 1-15; SPE 62919; Society of Petroleum Engineers, Inc.; Dallas, Texas, U.S.A.

Robert C. Earlougher, Jr.; "Advances In Well Test Analysis"; Society of Petroleum Engineers of AIME; 1997; New York, New York, U.S. A. and Dallas, Texas, U.S.A.

John Michaels et al.; "Advances in Wireline Formation Testing"; SPWLA 36th Annual Logging Symposium; Jun. 26-29, 1995; pp. 1-11.

Amit K. Sakar et al.; "Adverse Effects of Poor Mud Cake Quality: Supercharging and Fluid Sampling Study"; SPE Reservoir Eval. & Eng. 3 (3), Jun. 2000; pp. 256-262; Society of Petroleum Engineers, Inc.; U.S.A.

E. B. Dussan V. et al.; "An Analysis of the Pressure Response of a Single-Probe Formation Tester"; 62nd Annual Technical Conference and Exhibition; Sep. 27-30, 1987; pp. 519-527; SPE 16801; Society of Petroleum Engineers, Inc.; Dallas, Texas, U.S.A.

Ekrem Kasa;; "Analysis of Wireline Formation Test Data From Gas and Non-Darcy Flow Conditions"; 1998 SPE Permian Basin Oil and Gas Recovery Conference; Mar. 25-27, 1998; pp. 183-189; SPE 39769; Society of Petroleum Engineers, Inc.; Midland, Texas, U.S.A.

T. Zimmerman et al.; "Application of Emerging Wireline Formation Testing Technologies"; Eighth Offshore South East Asia Conference; Dec. 4-7, 1990; pp. 83-95; OSEA 90105; Offshore South East Asia; Singapore.

M. Hooper et al.; "Applications for an LWD Formation Tester"; 1999 SPE European Formation Damage Conference; May 28-Jun. 1, 1999; pp. 1-8; SPE 52794; Society of Petroleum Engineers, Inc.; The Hague, The Netherlands.

Cosan Ayan et al.; "Characterizing Permeability with Formation Testers"; Oilfield Review, Autumn 2001; pp. 2-23.

H. Elshahawi et al.; "Correcting for Wettability and Capillary Pressure Effects on Formation Tester Measurements"; SPWLA 41$^{st}$ Annual Logging Symposium; Jun. 4-7, 2000; pp. 1-14; Society of Petroleum Well Log Analysts; Dallas, Texas, U.S.A.

H. Elshahawi et al.; "Correcting for Wettability and Capillary Pressure Effects on Formation Tester Measurements"; 2000 SPE Annual Technical Conference and Exhibition; Oct. 1-4, 2000; pp. 1-15; SPE 63075; Society of Petroleum Engineers, Inc.; Dallas, Texas, U.S.A.

Jaedong Lee et al.; "Enhanced Wireline Formation Tests in Low-Permeability Formations: Quality Control Through Formation Rate Analysis"; 2000 SPE Rocky Mountain Regional/Low Permeability Reservoirs Symposium and Exhibition; Mar. 12-15, 2000; pp. 1-4 with Figures 1A-15; SPE 60392; Society of Petroleum Engineers Inc.; Denver, Colorado, U.S.A.

H. Badaam et al.; "Estimation of Formation Properties Using Multiprobe Formation Tester in Layered Reservoirs"; 1998 SPE Annual Technical Conference and Exhibition; Sep. 27-30, 1998; pp. 479-490; SPE 49141; Society of Petroleum Engineers, Inc.; New Orleans, Louisiana, U.S.A.

Long Haitao; "Follow-Up Monitoring and Evaluation of the Formation Pressure in the Process of Drilling"; Natur. Gas Ind., vol. 20, No. 4, pp. 33-36; Jul. 25, 2000. (Partial translation attached).

M. Meister et al.; "Formation Pressure Testing During Drilling: Challenges and Benefits"; SPE Annual Technical Conference and Exhibition; Oct. 5-8, 2003; pp. 1-8; SPE 84088; Society of Petroleum Engineers, Inc.; Denver, CO, U.S.A.

Mark Proett et al.; "Formation Pressure Testing In The Dynamic Drilling Environment"; 2004 IADC/SPE Drilling Conference; Mar. 2-4, 2004; pp. 1-11; IADC/SPE 87090; Society of Petroleum Engineers, Inc.; Dallas, Texas, U.S.A.

C. Frimann-Dahl et al.; "Formation Testers vs DST—The Cost Effective Use of Transient Analysis to Get Reservoir Parameters"; 1998 SPE Annual Technical Conference; Sep. 27-30, 1998; pp. 1-14; SPE 48962; Society of Petroleum Engineers, Inc.; New Orleans, Louisiana, U.S.A.

P.S. Varlamov et al.; "Formation Testing During Deep Well Drilling"; 1983; pp. 118-124; No. 39; Russia. (Partial translation attached).

Peter A. Goode et al.; "Influence of an Invaded Zone on a Multiprobe Formation Tester"; SPE Formation Evaluation, Mar. 1996; pp. 31-40.

Alastair Crombie et al.; "Innovations in Wireline Fluid Sampling"; pp. 26-41; Oilfield Review, Autumn 1998.

R. Desbrandes; "Invasion Diameter and Supercharging in Time-Lapse MWD/LWD Logging"; Proceedings, Measurement While Drilling Symposium; Feb. 26-27, 1990; pp. 115-135; Louisiana State University; Baton Rouge, Louisiana, U.S.A.

Mark A. Proett et al.; "Low Permeability Interpretation Using a New Wireline Formation Tester 'Tight Zone' Pressure Transient Analysis"; 1994 SPWLA 35th Annual Logging Symposium; Jun. 19-22, 1994; pp. 1-25.

R. Desbrandes et al.; "Measurement While Drilling"; Studies in Abnormal Pressures. Developments in Petroleum Science, 38; 1994; pp. 251-279; Elsevier Science B.V.

Mark A. Proett et al.; "Multiple Factors That Influence Wireline Formation Tester Pressure Measurements and Fluid Contact Estimates"; 2001 SPE Annual Technical Conference and Exhibition; Sep. 30-Oct. 3, 2001; pp. 1-16; SPE 71566; Society of Petroleum Engineers, Inc.; New Orleans, Louisiana, U.S.A.

Mark A. Proett et al.; "New Dual-Probe Wireline Formation Testing and Sampling Tool Enables Real-Time Permeability and Anistropy Measurements"; 2000 SPE Permian Basin Oil and Gas Recovery Conference; Mar. 21-23, 2000; pp. 1-16; SPE 59701; Society of Petroleum Engineers, Inc.; Midland, Texas, U.S.A.

Mark A. Proett et al.; "New Exact Spherical Flow Solution With Storage and Skin For Early-Time Interpretation With Applications to Wireline Formation and Early-Evaluation Drillstem Testing"; 1998 SPE Annual Technical Conference and Exhibition; Sep. 27-30, 1998; pp. 463-478; SPE 49140; Society of Petroleum Engineers, Inc.; New Orleans, Louisiana, U.S.A.

Mark A. Proett et al.; "New Exact Spherical Flow Solution With Storage For Early-Time Interpretation With Applications to Early-Evaluation Drillstem Testing and Wireline Formation Testing"; 1998 SPE Permian Basin Oil and Gas Recovery Conference; Mar. 25-27, 1998; pp. 167-181; SPE 39768; Society of Petroleum Engineers, Inc.; Midland, Texas, U.S.A.

Rob Badry et al.; "New Wireline Formation Tester Techniques and Applications"; 1993 SPWLA Annual Symposium; Jun. 13-16, 1993; pp. 1-15; Calgary, Alberta, Canada.

Mark A. Proett et al.; "New Wireline Formation Testing Tool With Advanced Sampling Technology"; 1999 SPE Annual Technical Conference and Exhibition; Oct. 3-6, 1999; pp. 1-16; SPE 56711; Society of Petroleum Engineers, Inc.; Houston, Texas, U.S.A.

A. F. Shakirov et al.; "On The Regimes of Formation Testing In Wells"; Neft Khoz; Dec. 1973; pp. 14-17; No. 12; Russia.

K. Zainun et al.; "Optimized Exploration Resource Evaluation Using the MDT Tool"; 1995 SPE Asia Pacific Oil and Gas Conference; Mar. 20-22, 1995; pp. 177-194; SPE 29270; Society of Petroleum Engineers, Inc.; Kuala Lumpur, Malaysia.

V. D. Banchenko et al.; "Results of Using Strata Testers Mounted on Tubes Lowered Into Boreholes in the Southern Mangyshlak Field"; 1982; pp. 28-29; No. 8; ISSN-0521-8136; Burenie; Russia (Partial translation attached).

E. Kasap et al.; "Robust and Simple Graphical Solution For Wireline Formation Tests: Combined Drawdown and Buildup Analyses"; 1996 SPE Annual Technical Conference and Exhibition; Oct. 6-9, 1996; pp. 343-357; SPE 36525; Society of Petroleum Engineers, Inc.; Denver, Colorado, U.S.A.

S. Haddad et al.; "So What Is The Reservoir Permeability?"; 2000 SPE Annual Technical Conference and Exhibition; Oct. 1-4, 2000; pp. 1-13; SPE 63138; Society of Petroleum Engineers, Inc.; Dallas, Texas, U.S.A.

P. Cooke-Yarborough; "Some 'Quick-Look' and Wellsite Applications of Wireline Formation Testing Tools With Emphasis on Permeability Indicators as an Aid to Choosing Net Pay Discriminations"; Proceedings Indonesian Petroleum Association; Thirteenth Annual Convention; May 1994; pp. 1-16.

Mark A. Proett et al.; "Supercharge Pressure Compensation Using a New Wireline Testing Method and Newly Developed Early Time Spherical Flow Model"; 1996 SPE Annual Technical Conference and Exhibition; Oct. 6-9, 1996; pp. 329-342; SPE 36524; Society of Petroleum Engineers, Inc.; Denver, Colorado, U.S.A.

G.D. Phelps et al.; "The Analysis of the Invaded Zone Characteristics and Their Influence on Wireline Log and Well-Test Interpretation"; 1984 Society of Petroleum Engineers of AIME 59th Annual Conference and Exhibition; Sep. 16-19, 1984; pp. 1-10; Tables 1-4; Figures 1-14; SPE 13287; Society of Petroleum Engineers of AIME; Houston, Texas, U.S.A.

D.K. Sethi et al.; "The Formation Multi-Tester: Its Basic Principles and Practical Field Applications"; SPWLA Twenty-First Annual Logging Symposium; Jul. 8-11, 1980; pp. 1-34.

M.M. Kamal et al.; "Use of Transient Testing in Reservoir Management"; University of Tulsa Centennial Petroleum Engineering Symposium; Aug. 29-31, 1994; pp. 519-531; SPE 28008; Society of Petroleum Engineers; Tulsa, Oklahoma, U.S.A.

"Well Testing Using Wireline Methods"; Schlumberger East Asia Well Evaluation Conference; 1981; pp. 121-144; Singapore.

R. Desbrandes et al.; "Wettability and Productivity Characterization of Low Permeability Gas Formations: Annual Report"; Gas Research Institute; Report GRI-91/0135; Mar. 6, 1991.

J. Michaels et al.; "Wireline Fluid Sampling"; 1995 SPE Annual Technical Conference and Exhibition; Oct. 22-25, 2005; pp. 871-878; SPE 36010; Society of Petroleum Engineers, Inc.; Dallas, Texas, U.S.A.

E. C. Thomas; "Wireline Formation Tester Data: Fact or Fiction?"; Petrophysics, vol. 41, No. 5, Sep.-Oct. 2000; pp. 375-378.

R. Desbrandes; "Wireline Formation Testing: A New Extended Drawdown Technique"; Petroleum Engineer International; pp. 40-44; May 1991.

PCT International Search Report dated Jan. 3, 2007.

PCT International Search Report dated Nov. 10, 2005.

* cited by examiner

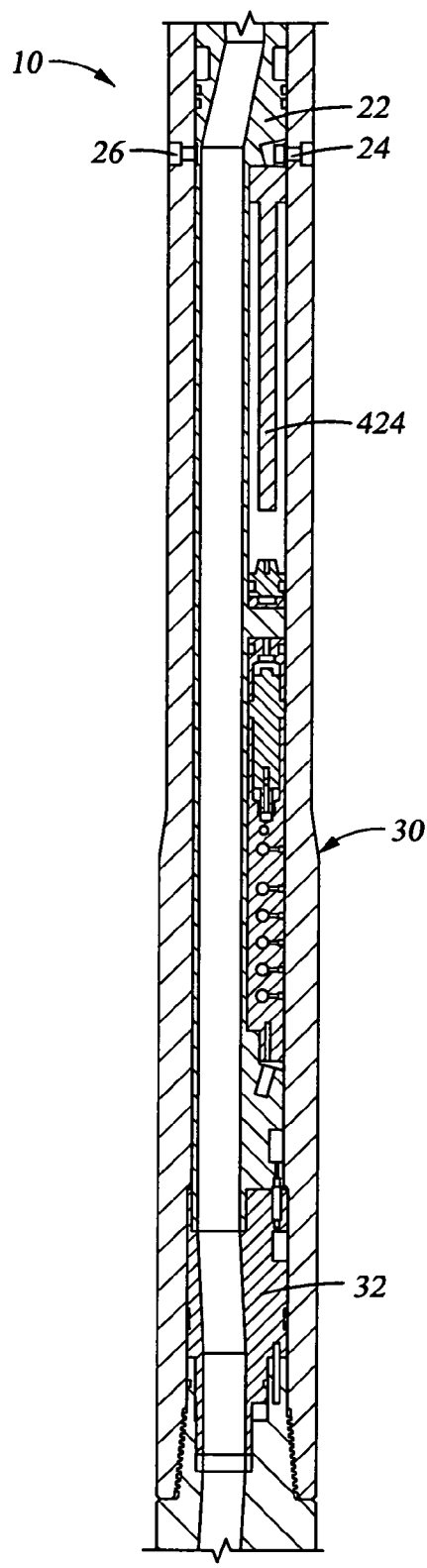
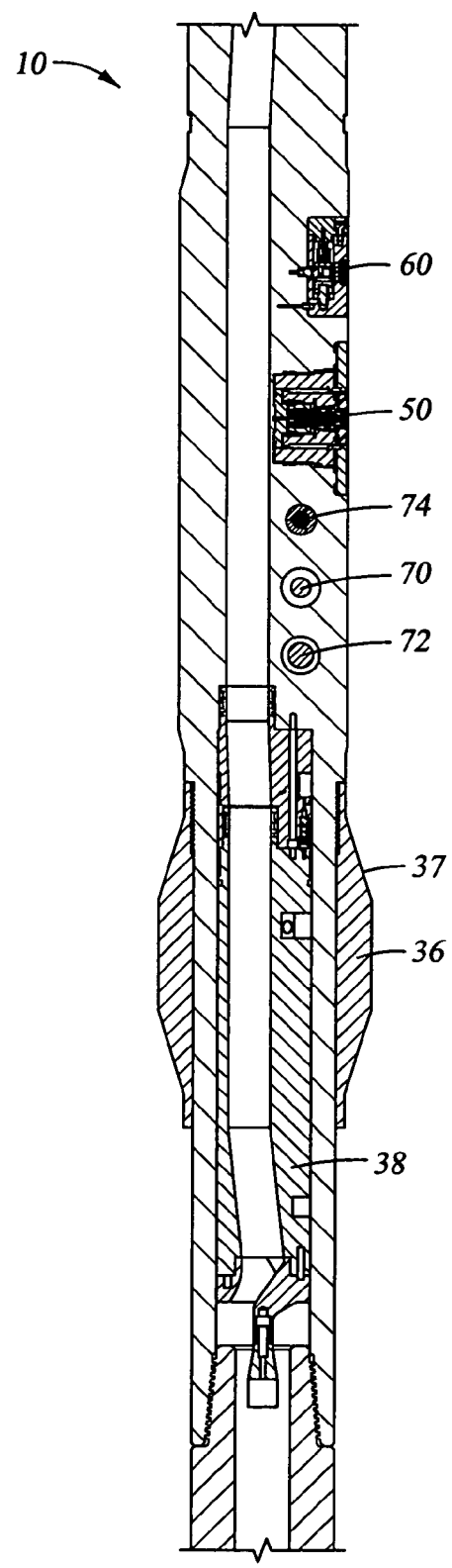
Fig. 3A
Fig. 3B

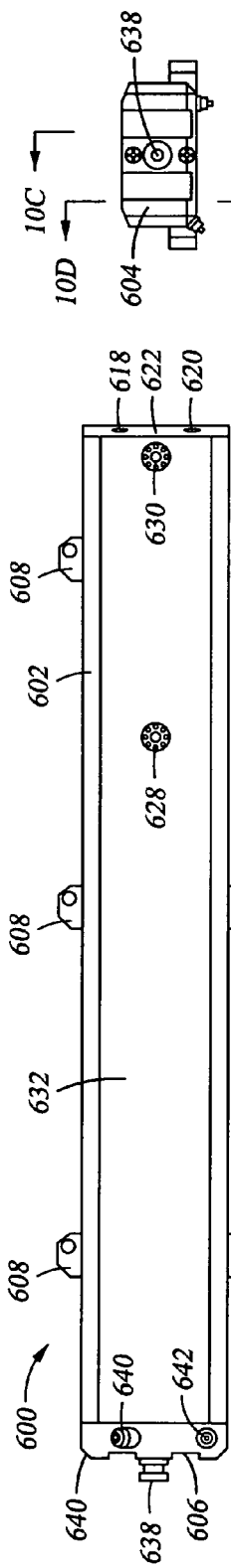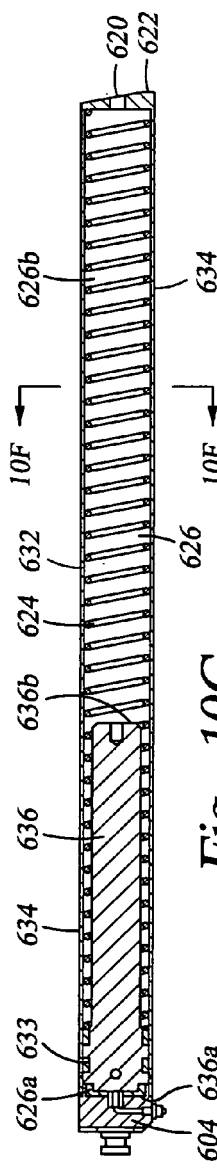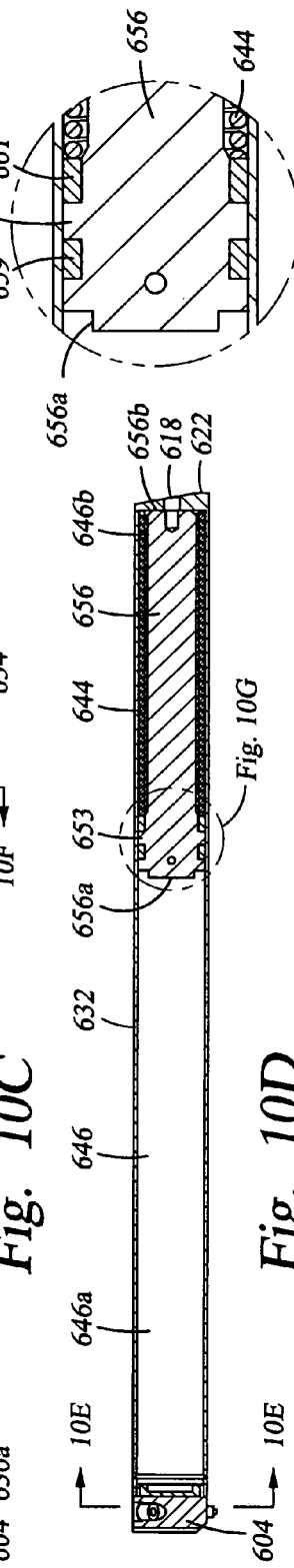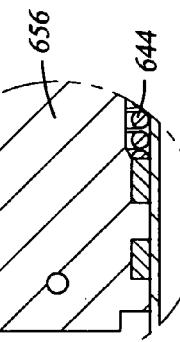

DOWNHOLE PROBE ASSEMBLY

CROSS-REFERENCE TO RELATED APPLICATIONS

The present application claims the benefit of U.S. Provisional Application Ser. No. 60/573,294, filed May 21, 2004, entitled Downhole Probe Assembly, which is hereby incorporated herein by reference.

STATEMENT REGARDING FEDERALLY SPONSORED RESEARCH OR DEVELOPMENT

Not applicable.

BACKGROUND

During the drilling and completion of oil and gas wells, it may be necessary to engage in ancillary operations, such as monitoring the operability of equipment used during the drilling process or evaluating the production capabilities of formations intersected by the wellbore. For example, after a well or well interval has been drilled, zones of interest are often tested to determine various formation properties such as permeability, fluid type, fluid quality, formation temperature, formation pressure, bubblepoint and formation pressure gradient. These tests are performed in order to determine whether commercial exploitation of the intersected formations is viable and how to optimize production.

Wireline formation testers (WFT) and drill stem testing (DST) have been commonly used to perform these tests. The basic DST test tool consists of a packer or packers, valves or ports that may be opened and closed from the surface, and two or more pressure-recording devices. The tool is lowered on a work string to the zone to be tested. The packer or packers are set, and drilling fluid is evacuated to isolate the zone from the drilling fluid column. The valves or ports are then opened to allow flow from the formation to the tool for testing while the recorders chart static pressures. A sampling chamber traps clean formation fluids at the end of the test. WFTs generally employ the same testing techniques but use a wireline to lower the test tool into the well bore after the drill string has been retrieved from the well bore, although WFT technology is sometimes deployed on a pipe string. The wireline tool typically uses packers also, although the packers are placed closer together, compared to drill pipe conveyed testers, for more efficient formation testing. In some cases, packers are not used. In those instances, the testing tool is brought into contact with the intersected formation and testing is done without zonal isolation across the axial span of the circumference of the borehole wall.

WFTs may also include a probe assembly for engaging the borehole wall and acquiring formation fluid samples. The probe assembly may include an isolation pad to engage the borehole wall. The isolation pad seals against the formation and around a hollow probe, which places an internal cavity in fluid communication with the formation. This creates a fluid pathway that allows formation fluid to flow between the formation and the formation tester while isolated from the borehole fluid.

In order to acquire a useful sample, the probe must stay isolated from the relative high pressure of the borehole fluid. Therefore, the integrity of the seal that is formed by the isolation pad is critical to the performance of the tool. If the borehole fluid is allowed to leak into the collected formation fluids, a non-representative sample will be obtained and the test will have to be repeated.

With the use of WFTs and DSTs, the drill string with the drill bit must be retracted from the borehole. Then, a separate work string containing the testing equipment, or, with WFTs, the wireline tool string, must be lowered into the well to conduct secondary operations. Interrupting the drilling process to perform formation testing can add significant amounts of time to a drilling program.

DSTs and WFTs may also cause tool sticking or formation damage. There may also be difficulties of running WFTs in highly deviated and extended reach wells. WFTs also do not have flowbores for the flow of drilling mud, nor are they designed to withstand drilling loads such as torque and weight on bit.

Further, the formation pressure measurement accuracy of drill stem tests and, especially, of wireline formation tests may be affected by filtrate invasion and mudcake buildup because significant amounts of time may have passed before a DST or WFT engages the formation. Mud filtrate invasion occurs when the drilling mud fluids displace formation fluids. Because the mud filtrate ingress into the formation begins at the borehole surface, it is most prevalent there and generally decreases further into the formation. When filtrate invasion occurs, it may become impossible to obtain a representative sample of formation fluids or, at a minimum, the duration of the sampling period must be increased to first remove the drilling fluid and then obtain a representative sample of formation fluids. The mudcake is made up of the solid particles that are deposited on the side of the well as the filtrate invades the near well bore during drilling. The prevalence of the mudcake at the borehole surface creates a "skin." Thus there may be a "skin effect" because formation testers can only withdraw fluids from relatively short distances into the formation, thereby distorting the representative sample of formation fluids due to the filtrate. The mudcake also acts as a region of reduced permeability adjacent to the borehole. Thus, once the mudcake forms, the accuracy of reservoir pressure measurements decreases, affecting the calculations for permeability and producibility of the formation.

Another testing apparatus is the measurement while drilling (MWD) or logging while drilling (LWD) tester. Typical LWD/MWD formation testing equipment is suitable for integration with a drill string during drilling operations. Various devices or systems are provided for isolating a formation from the remainder of the wellbore, drawing fluid from the formation, and measuring physical properties of the fluid and the formation. With LWD/MWD testers, the testing equipment is subject to harsh conditions in the wellbore during the drilling process that can damage and degrade the formation testing equipment before and during the testing process. These harsh conditions include vibration and torque from the drill bit, exposure to drilling mud, drilled cuttings, and formation fluids, hydraulic forces of the circulating drilling mud, and scraping of the formation testing equipment against the sides of the wellbore. Sensitive electronics and sensors must be robust enough to withstand the pressures and temperatures, and especially the extreme vibration and shock conditions of the drilling environment, yet maintain accuracy, repeatability, and reliability.

BRIEF DESCRIPTION OF THE DRAWINGS

For a more detailed description of preferred embodiments of the present invention, reference will now be made to the accompanying drawings, wherein:

FIGS. 3A-3B are enlarged elevation views, in cross-section, of the formation tester tool portion of the formation tester assembly shown in FIGS. 2B-2C;

FIG. 10A is a top elevation view of a hydraulic reservoir accumulator assembly employed in the formation tester assembly;

FIG. 10B is an end view of the reservoir accumulator assembly of FIG. 10A;

FIG. 10C is a cross-section view taken along line C-C of FIG. 10B;

FIG. 10D is a cross-section view taken along line D-D of FIG. 10B;

FIG. 10E is a cross-section view taken along line E-E of FIG. 10D;

FIG. 10F is a cross-section view taken along line F-F of FIG. 10C;

FIG. 10G is an enlarged view of the detail of FIG. 10D;

DETAILED DESCRIPTION OF PREFERRED EMBODIMENTS

Figure 1:
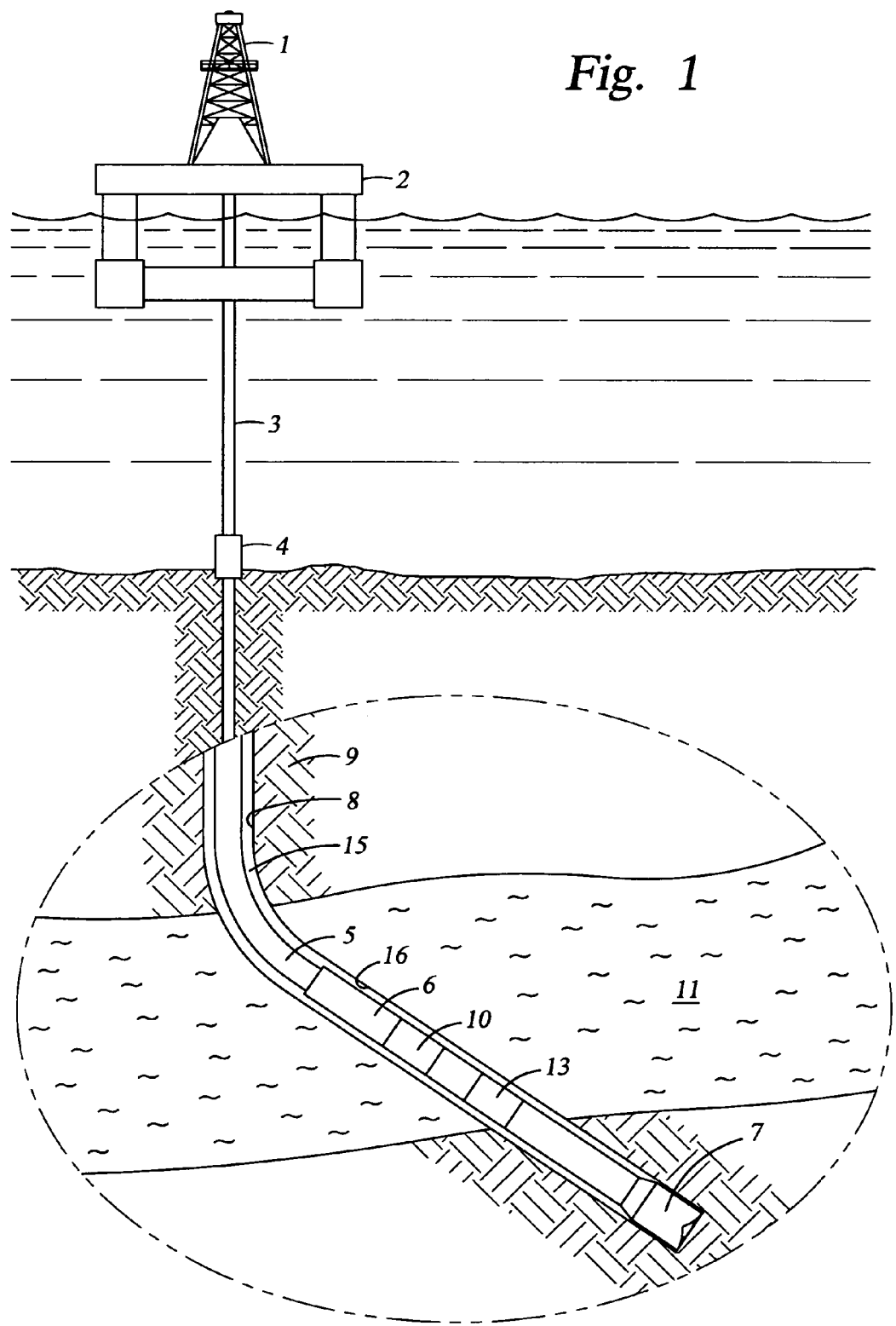
FIG. 1 is a schematic elevation view, partly in cross-section, of an embodiment of a formation tester apparatus disposed in a subterranean well.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the terms "couple," "couples", and "coupled" used to describe any electrical connections are each intended to mean and refer to either an indirect or a direct electrical connection. Thus, for example, if a first device "couples" or is "coupled" to a second device, that interconnection may be through an electrical conductor directly interconnecting the two devices, or through an indirect electrical connection via other devices, conductors and connections. Further, reference to "up" or "down" are made for purposes of ease of description with "up" meaning towards the surface of the borehole and "down" meaning towards the bottom or distal end of the borehole. In addition, in the discussion and claims that follow, it may be sometimes stated that certain components or elements are in fluid communication. By this it is meant that the components are constructed and interrelated such that a fluid could be communicated between them, as via a passageway, tube, or conduit. Also, the designation "MWD" or "LWD" are used to mean all generic measurement while drilling or logging while drilling apparatus and systems.

To understand the mechanics of formation testing, it is important to first understand how hydrocarbons are stored in subterranean formations. Hydrocarbons are not typically located in large underground pools, but are instead found within very small holes, or pore spaces, within certain types of rock. Therefore, it is critical to know certain properties of both the formation and the fluid contained therein. At various times during the following discussion, certain formation and formation fluid properties will be referred to in a general sense. Such formation properties include, but are not limited to: pressure, permeability, viscosity, mobility, spherical mobility, porosity, saturation, coupled compressibility porosity, skin damage, and anisotropy. Such formation fluid properties include, but are not limited to: viscosity, compressibility, flowline fluid compressibility, density, resistivity, composition and bubble point.

Permeability is the ability of a rock formation to allow hydrocarbons to move between its pores, and consequently into a wellbore. Fluid viscosity is a measure of the ability of the hydrocarbons to flow, and the permeability divided by the viscosity is termed "mobility." Porosity is the ratio of void space to the bulk volume of rock formation containing that void space. Saturation is the fraction or percentage of the pore volume occupied by a specific fluid (e.g., oil, gas, water, etc.). Skin damage is an indication of how the mud filtrate or mud cake has changed the permeability near the wellbore. Anisotropy is the ratio of the vertical and horizontal permeabilities of the formation.

Resistivity of a fluid is the property of the fluid which resists the flow of electrical current. Bubble point occurs when a fluid's pressure is brought down at such a rapid rate, and to a low enough pressure, that the fluid, or portions thereof, changes phase to a gas. The dissolved gases in the fluid are brought out of the fluid so gas is present in the fluid in an undissolved state. Typically, this kind of phase change in the formation hydrocarbons being tested and measured is undesirable, unless the bubblepoint test is being administered to determine what the bubblepoint pressure is.

In the drawings and description that follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results. The various characteristics mentioned above, as well as other features and characteristics described in more detail below, will be readily apparent to those skilled in the art upon reading the following detailed description of the embodiments, and by referring to the accompanying drawings.

Referring to FIG. 1, a formation tester tool 10 is shown as a part of bottom hole assembly 6 which includes an MWD sub 13 and a drill bit 7 at its lower most end. Bottom hole assembly 6 is lowered from a drilling platform 2, such as a ship or other conventional platform, via drill string 5. Drill string 5 is disposed through riser 3 and well head 4. Conventional drilling equipment (not shown) is supported within derrick 1 and rotates drill string 5 and drill bit 7, causing bit 7 to form a borehole 8 through the formation material 9. The borehole 8 penetrates subterranean zones or reservoirs, such as reservoir 11, that are believed to contain hydrocarbons in a commercially viable quantity. It should be understood that formation tester 10 may be employed in other bottom hole assemblies and with other drilling apparatus in land-based drilling, as well as offshore drilling as shown in FIG. 1. In all instances, in addition to formation tester 10, the bottom hole assembly 6 contains various conventional apparatus and systems, such as a down hole drill motor, rotary steerable tool, mud pulse telemetry system, measurement-while-drilling sensors and systems, and others well known in the art.

It should also be understood that, even though formation tester 10 is shown as part of drill string 5, the embodiments of the invention described below may be conveyed down borehole 8 via wireline technology, as is partially described above, or via a rotary steerable drill string that is well known to one skilled in the art. Further context and examples for methods of use of the embodiments described herein may be obtained from U.S. patent application Ser. No. 11/133,712 entitled "Formation Tester Tool Assembly and Methods of Use," having U.S. Express Mail Label Number EV 303483552 US; U.S. patent application Ser. No. 11/132,475 entitled "Methods for Using a Formation Tester," having U.S. Express Mail Label Number EV 303483362 US; and U.S. patent application entitled "Methods for Measuring a Formation Supercharge Pressure," having U.S. patent application Ser. No. 11/069,649; each hereby incorporated herein by reference for all purposes.

Figure 2A:
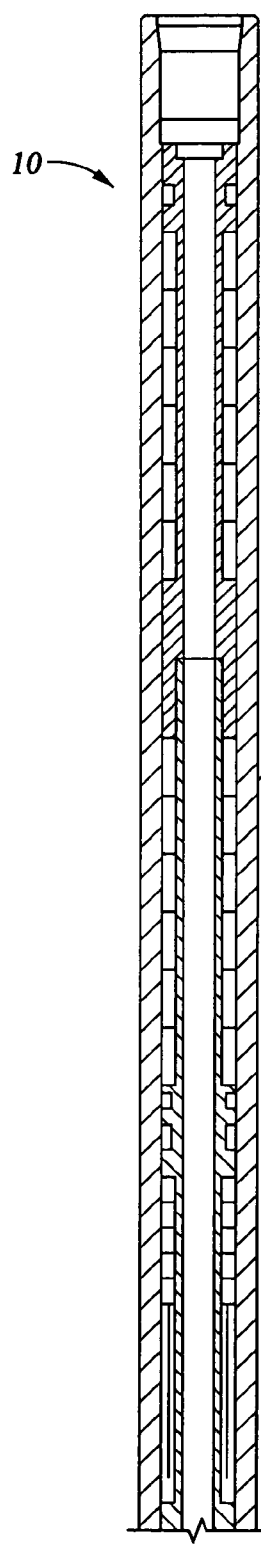
FIGS. 2A-2C are elevation views, in cross-section, of portions of the bottomhole assembly and formation tester assembly shown in FIG. 1.
Figure 2B:
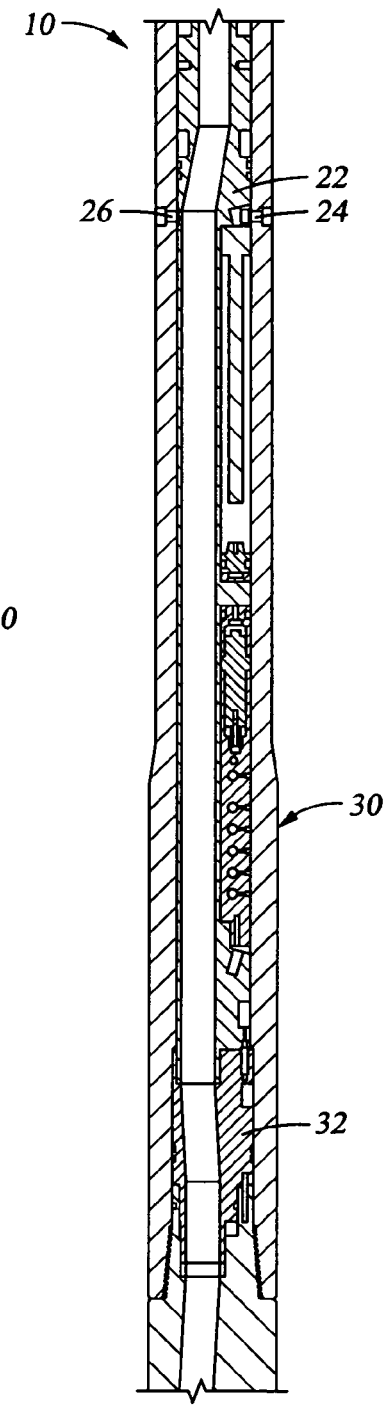
Figure 2C:
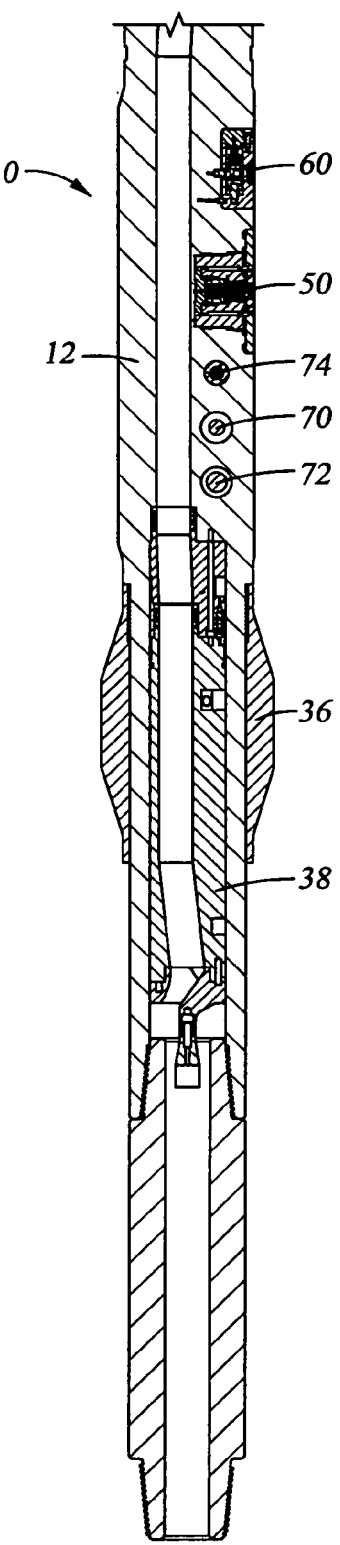

Referring now to FIGS. 2A-C, portions of the formation tester tool 10 are shown. FIG. 2A illustrates the electronics module 20, which may include battery packs, various circuit boards, capacitors banks and other electrical components. FIG. 2B shows fillport assembly 22 having fillports 24, 26 for adding or removing hydraulic or other fluids to the tool 10. Below fillport assembly 22 is hydraulic insert assembly 30. Below assembly 30 is the hydraulic connectors ring assembly 32, which acts as a hydraulic line manifold. FIG. 2C illustrates the portion of tool 10 including equalizer valve 60, formation probe assembly 50 (or probe assembly 200), draw down shutoff valve assembly 74, draw down piston assemblies 70, 72 and stabilizer 36. Also included is pressure instrument assembly 38, including the pressure transducers used by formation probe assemblies 50, 200.

Referring to FIGS. 3A-B now, the enlarged portions of tool 10 shown in FIGS. 2B-C are shown. Hydraulic insert assembly 30, probe retract accumulator 424, equalizer valve 60, formation probe assembly 50, draw down shutoff valve 74 and draw down piston assemblies 70, 72 can be seen in greater detail. Equalizer valve 60 may be any of a variety of equalizer valves known to one skilled in the art.

Figure 4:
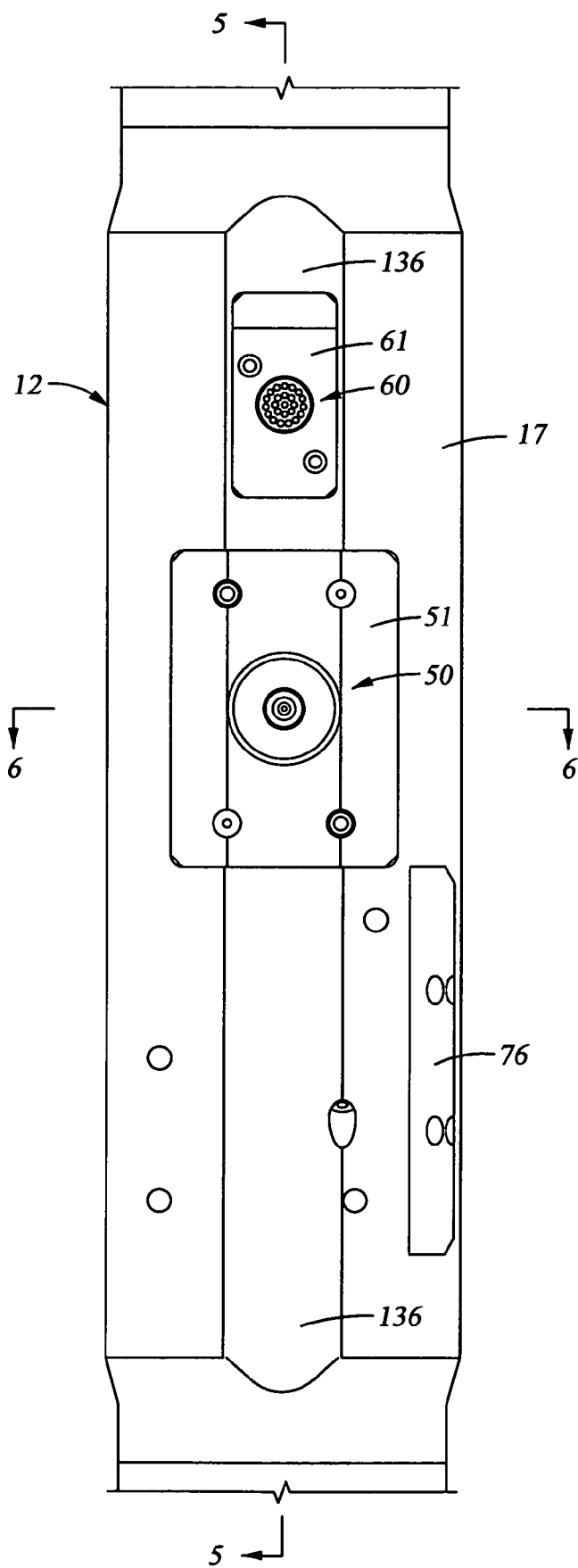
FIG. 4 is an elevation view of the formation probe assembly and equalizer valve collar shown in FIG. 3B.

Referring now to FIG. 4, formation probe assembly 50 is disposed within probe drill collar 12, and covered by probe cover plate 51. Also disposed within probe collar 12 is an equalizer valve 60 having a valve cover plate 61. Adjacent formation probe assembly 50 and equalizer valve 60 is a flat 136 in the surface 17 of probe collar 12. Probe drill collar 12 includes a draw down cover 76 for protecting other devices associated with the formation probe assembly 50 mounted in the collar 12, such as draw down pistons (not shown).

Figure 5:
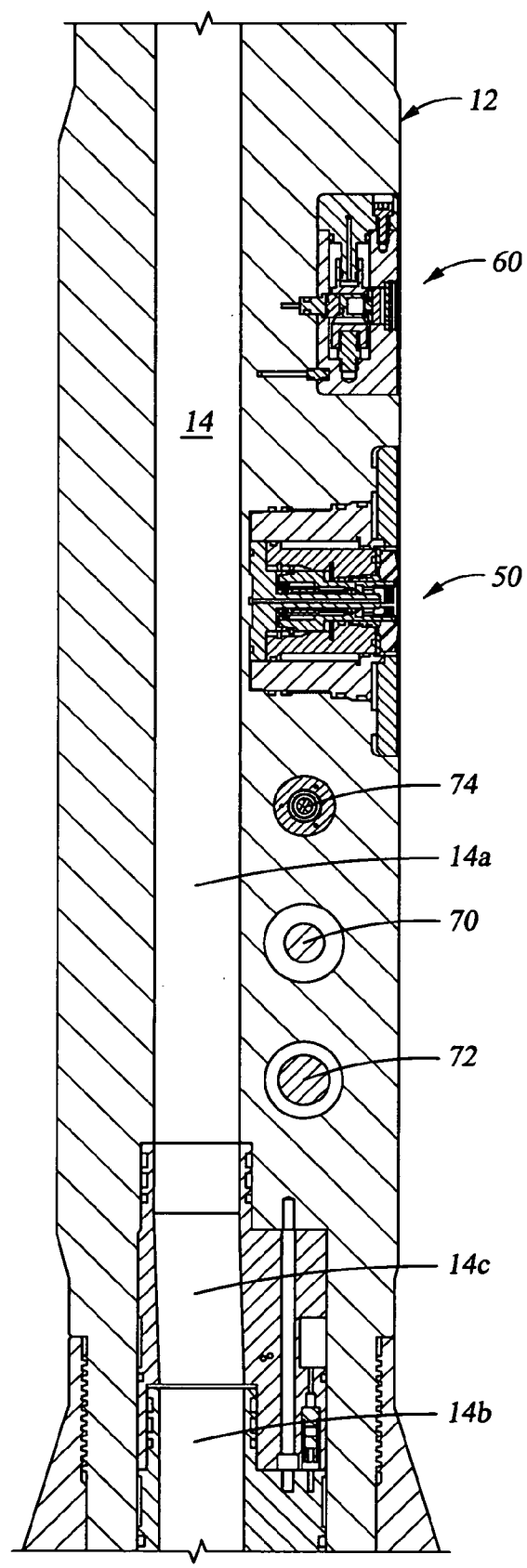
FIG. 5 is an enlarged cross-section view along line 5-5 of FIG. 4.

As best shown in FIG. 5, it can be seen how formation probe assembly 50 and equalizer valve 60 are positioned in probe collar 12. Formation probe assembly 50 and equalizer valve 60 are mounted in probe collar 12 just above the flowbore 14. Flowbore 14 may be deviated from the center longitudinal axis 12a of probe collar 12, or from other portions 14b, 14c of flowbore 14, to accommodate at least formation probe assembly 50. For example, in FIG. 5, flowbore portion 14a is offset radially from the longitudinal axis 12a, and also from the flowbore portion 14b via transition flowbore portion 14c. Also shown are draw down piston assemblies 70, 72 and draw down shutoff valve 74.

Figure 6A:
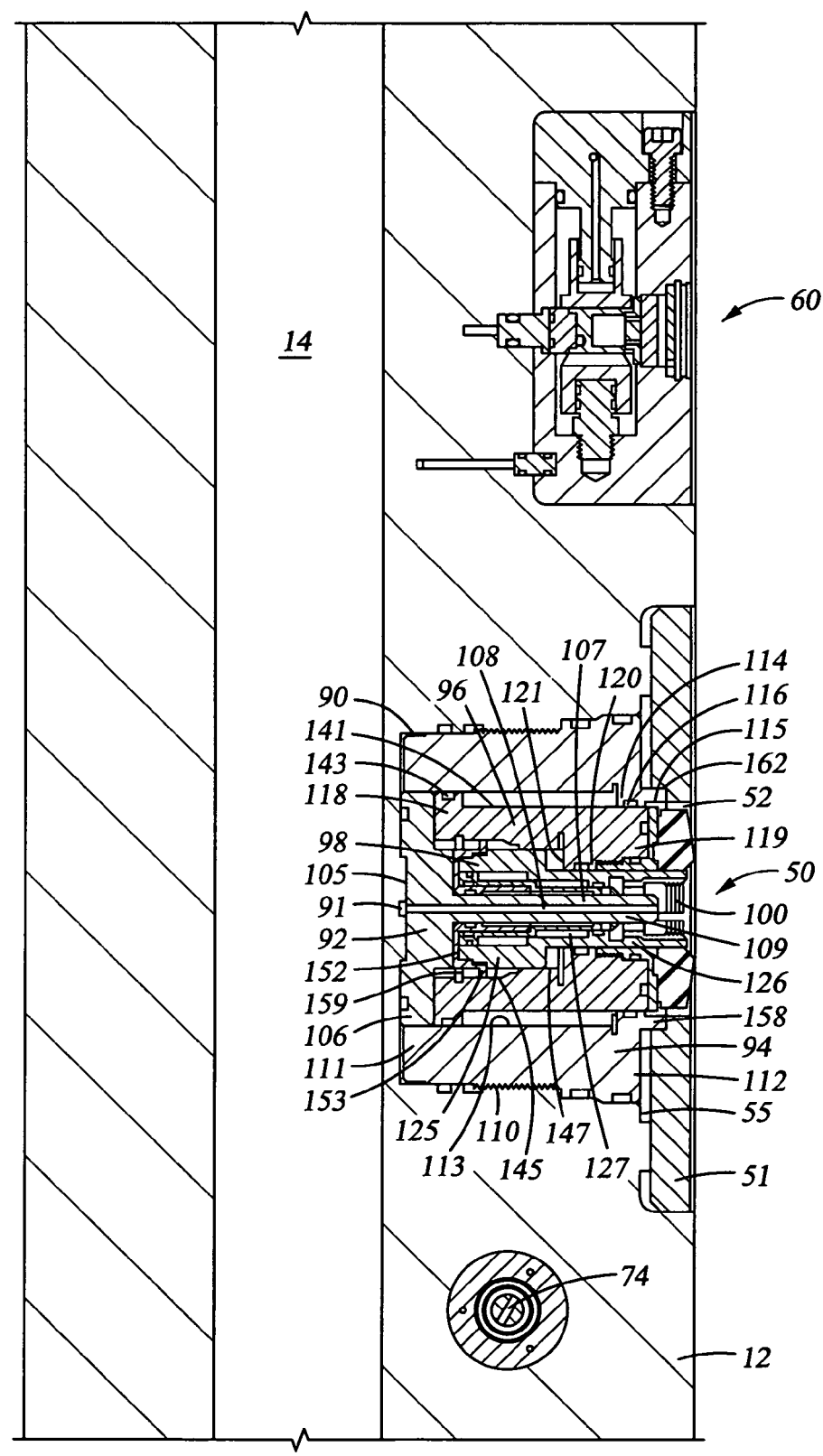
FIG. 6A is an enlarged view, in cross-section, of the formation probe assembly in a retracted position and equalizer valve shown in FIG. 5.
Figure 6B:
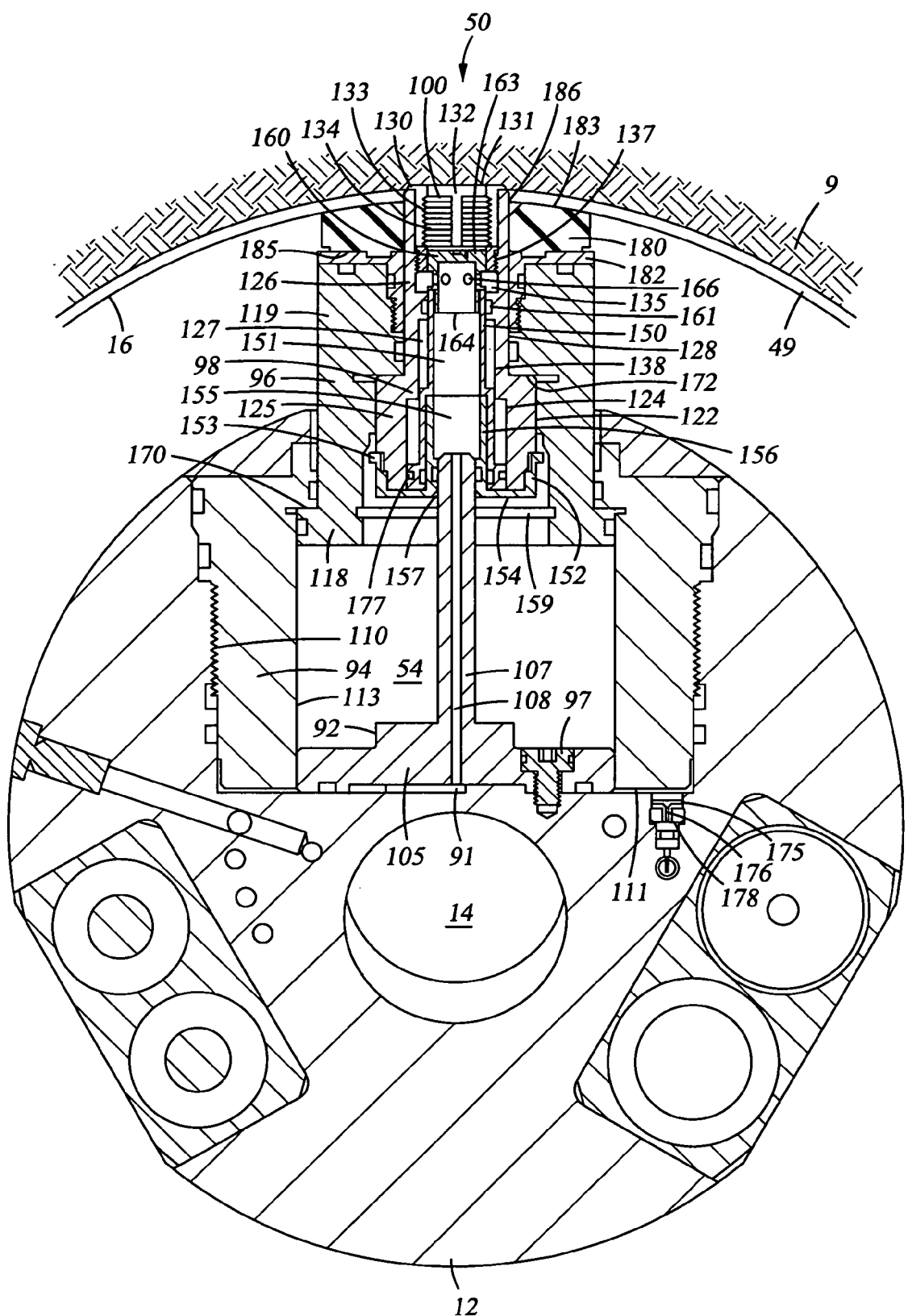
FIG. 6B is an enlarged view, in cross-section, of the formation probe assembly along line 6-6 of FIG. 4, the probe assembly being in an extended position.

The details of a first embodiment of formation probe assembly 50 are best shown in FIG. 6A-6B. In FIG. 6A, formation probe assembly 50 is retained in probe collar 12 by threaded engagement with collar 12 and also by cover plate 51. Formation probe assembly 50 generally includes stem 92, a generally cylindrical threaded adapter sleeve 94, piston 96 adapted to reciprocate within adapter sleeve 94, and a snorkel assembly 98 adapted for reciprocal movement within piston 96. Probe collar 12 includes an aperture 90 for receiving formation probe assembly 50. Cover plate 51 fits over the top of formation probe assembly 50 and retains and protects formation probe assembly 50 when the formation probe assembly 50 is within probe collar 12. Formation probe assembly 50 may extend and retract through aperture 52 in cover plate 51.

Stem 92 includes a circular base portion 105 with an outer flange 106 having stem holding screw 97 (shown in FIG. 6B) for retaining stem 92 in aperture 90. Extending from base 105 is a tubular extension 107 having central passageway 108. The end of extension 107 includes internal threads at 109. Central passageway 108 is in fluid connection with fluid passageway 91 (not shown, but seen schematically in FIG. 9) that connects to fluid passageway 93 (not shown, but seen schematically in FIG. 9) leading to other portions of tool 10, including equalizer valve 60.

Adapter sleeve 94 includes inner end 111 that engages flange 106 of stem 92. Adapter sleeve 94 is secured within aperture 90 by threaded engagement with collar 12 at segment 110. The outer end 112 of adapter sleeve 94 may extend to be substantially flushed with recess 55 formed in collar 12 for receiving cover plate 51. Outer end 112 also includes flange 158 for engaging recess 162 of cover plate 51. Adapter sleeve 94 includes cylindrical inner surface 113 having reduced diameter portions 114, 115. A seal 116 is disposed in surface 114.

Piston 96 is slidingly retained within adapter sleeve 94 and generally includes cylindrical outer surface 141 having an increased diameter base portion 118. A seal 143 is disposed in increased diameter portion 118. Just below base portion 118, piston 96 may rest on flange 106 of stem base portion 105 while formation probe assembly 50 is in the fully retracted position as shown in FIG. 6A. Piston 96 may also include cylindrical inner surface 145 having reduced diameter portion 147. Piston 96 may further include central bore 121 having a bore surface 120 and extending through upper extending portion 119.

Referring to FIG. 6B, at the top of extending portion 119 of piston 96 is a seal pad 180. Seal pad 180 may be donut-shaped with a curved outer sealing surface 183 and central aperture 186. However, seal pad 180 may include numerous other geometries as is known in the art, or, for example, as is seen in U.S. patent application Ser. No. 10/440,835 entitled "MWD Formation Tester." Base surface 185 of seal pad 180 may be coupled to a skirt 182. Seal pad 180 may be bonded to skirt 182, or otherwise coupled to skirt 182, such as by molding seal pad 180 onto skirt 182 such that the seal pad material fills grooves or holes in skirt 182, as can be seen in U.S. patent application Ser. No. 10/440,835. Skirt 182 is detachably coupled to extending portion 119 by way of threaded engagement with surface 120 of central bore 121 (see FIG. 6A), or other means of engagement, such as a pressure fit with central bore surface 120. Because the seal pad/skirt combination may be detachable from extending portion 119, it is easily replaced in the field. Alternatively, seal pad 180 may be coupled directly to extending portion 119 without using a skirt.

Seal pad 180 is preferably made of an elastomeric material. Seal pad 180 seals and prevents drilling fluid or other contaminants from entering the formation probe assembly 50 during formation testing. More specifically, seal pad 180 may seal against the filter cake that may form on a borehole wall. Typically, the pressure of the formation fluid is less than the pressure of the drilling fluids that are injected into the borehole. A layer of residue from the drilling fluid forms a filter cake on the borehole wall and separates the two pressure areas. Seal pad 180, when extended, may conform its shape to the borehole wall and/or mud cake and forms a seal through which formation fluids can be collected and/or formation properties measured.

In an alternative embodiment of the seal pad 180, the seal pad 180 may have an internal cavity such that it can retain a volume of fluid. A fluid may be pumped into the seal pad cavity at variable rates such that the pressure in the seal pad cavity may be increased and decreased. Fluids used to fill the seal pad may include hydraulic fluid, saline solution or silicone gel. By way of example, the seal pad may be emptied or unpressured as the probe extends to engage the borehole wall. Depending on the contour of the borehole wall, the seal pad may be pressured by filling the seal pad with fluid, thereby conforming the seal pad surface to the contour of the borehole wall and providing a better seal.

In yet another embodiment of the seal pad, the seal pad may be filled, either before or after engagement with the borehole wall, with an electro-rheological fluid. An electro-rheological fluid may be an insulating oil containing a dispersion of fine solid particles, for example, 5 μm to 50 μm in diameter. Such an electro-rheological fluid is well known in the art. When subjected to an electric field, theses fluids develop an increased shear stress and an increased static yield stress that make them more resistant to flow. This change of fluid properties is evident, for example, as an increase in viscosity, most notably the plastic viscosity, when the electric field is applied. The fluid in the seal pad may effectively become semi-solid. The semi-solid effect is reversed when the fluid is no longer subjected to the electric field. In the absence of the electric field, the electro-rheological fluid that may fill the seal pad becomes less viscous, causing the seal pad to conform to the contour of a borehole wall. Once the seal pad has conformed to the borehole wall, an electric field may be applied to the electro-rheological fluid inside the seal pad, causing an increase in fluid viscosity, a stiffening of the seal pad, and a better seal.

Still referring to FIG. 6B, snorkel assembly 98 includes a base portion 125, a snorkel extension 126, and a central passageway 127 extending through base 125 and extension 126. Base portion 125 may include a cylindrical outer surface 122 and inner surface 124. Extension 126 may include a cylindrical outer surface 128 and inner surface 138. Disposed inside the top of extension 126 is a screen 100. Screen 100 is a generally tubular member having a central bore 132 extending between a fluid inlet end 131 and fluid outlet end 135. Screen 100 further includes a flange 130 adjacent to fluid inlet end 131 and an internally slotted segment 133 having slots 134. Between slotted segment 133 and outlet end 135, screen 100 includes threaded segment 137 for threadedly engaging snorkel extension 126.

Threaded to the bottom of base portion 125 of snorkel 98 is scraper tube keeper 152 having a circular base portion 154 with flange 153, a tubular extension 156 having a central passageway 155 and a central aperture 157 for receiving stem extension 107. Just below scraper tube keeper 152 is retainer ring 159, which provides seated engagement with snorkel 98 such that the movement of snorkel 98 is limited in the retract direction. Scraper tube keeper 152 supports scraper tube 150 when scraper tube 150 is in the retracted position shown in FIG. 6B. Scraper tube 150 having central passageway 151 extends up from scraper tube keeper 152 and through passageway 127 of snorkel 98. Coupled at the top of scraper tube 150 is scraper or wiper 160. Scraper 160 is threadedly engaged with scraper tube 150 at threaded segment 161. Scraper 160 is a generally cylindrical member including scraper plug portion 163, central bore 164 and apertures 166 that are in fluid communication with central bore 164. Scraper 160 is disposed within central bore 132 of screen 100 and may be actuated back and forth (or reciprocal) between screen inlet end 131 and outlet end 135. When scraper tube 150 and scraper 160 are in their retracted positions, as shown in FIG. 6B, apertures 166 are in fluid communication with fluid outlet end 135 of screen 100, thereby allowing fluid to pass from screen 100, through scraper bore 164, and into central passageway 155 of scraper tube 150. Scraper or wiper 160 is thus configured to be a moveable or floating scraper.

In an alternative embodiment of the scraper 160 within the screen 100, the actuation of scraper 160 may be a rotational movement around the longitudinal axis of scraper 160. This rotational movement may be in place of the reciprocal movement, or in addition to the reciprocal movement.

Figure 8A:
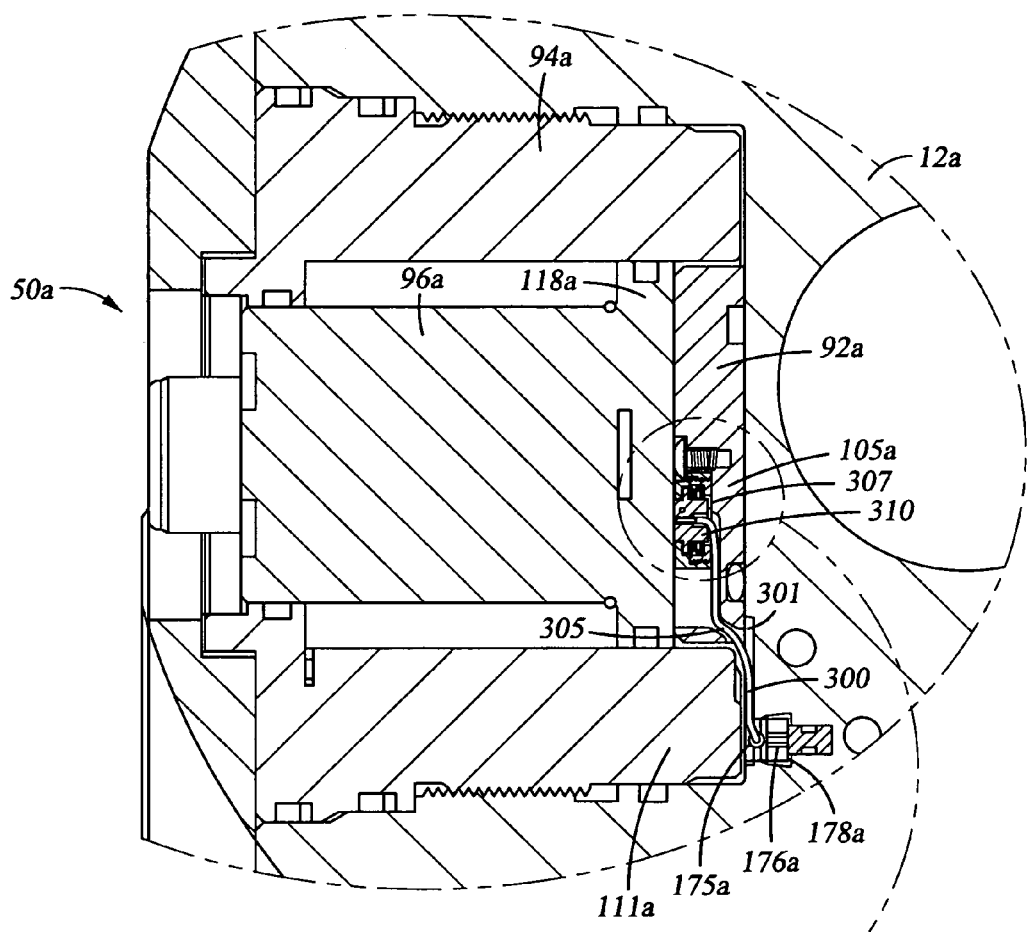
FIG. 8A is a schematic elevation view, in cross-section, of the probe retract switch portion of the formation probe assembly.
Figure 8B:
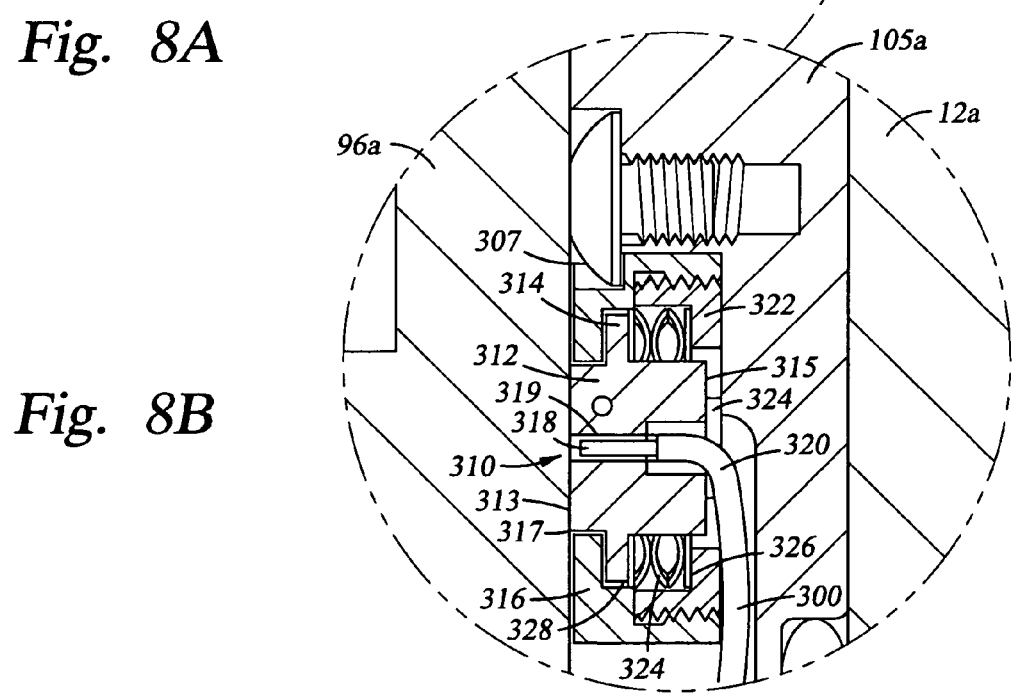
FIG. 8B is an enlarged view of the contact portion of the retract switch shown in FIG. 8A.

As shown in FIG. 6B, a connector 176 is disposed in aperture 178 of probe collar 12, just beneath inner end 111 of sleeve 94. Contact lead 175 electrically connects connector 176, via a wire, to a contact assembly (not shown) preferably disposed in flange 106 of stem base portion 105 so that the contact assembly can be in direct contact with base portion 118 of piston 96. FIGS. 8A-8B show the details of connector 176 and contact assembly 310, with the surrounding structures shown in a more general fashion such that the different parts of formation probe assembly 50a generally correspond with similar parts of formation probe assembly 50 of FIGS. 6A-6B.

Referring first to FIG. 8A, connector 176a is disposed in aperture 178a in probe collar 12a. Contact lead 175a is coupled to wire 300, which extends through recess 301 in collar 12a to opening 305 in base portion 105a of stem 92a. From opening 305, wire 300 extends through base portion 105a to a cavity 307, where contact assembly 310 is disposed.

Referring now to FIG. 8B, wire 300 leads into contact assembly 310. Contact assembly 310 generally includes housing 316 having aperture 317, a conductive contact body 312 having a flange 314 and a central bore 319, a stripped end 318 of wire 300 extending into and soldered to bore 319, a non-conductive spring support 322, and wave springs 324. The flange 314 of body 312 is disposed between the upper portion of housing 316 and the lower portion of spring support 322. Disposed between spring support 322 and flange 314 are wave springs 324, which are supported by lower plate 326 and upper plate 328. Springs 324 provide an upward force on flange 314 such that top surface 313 of body 312 extends out of aperture 317 such that top surface 313 protrudes out of cavity 307. As formation probe assembly 50a is retracting, piston 96a comes into contact with and presses downward on surface 313 of body 312, causing springs 324 to compress and bottom surface 315 to move downward into space 324. When piston 96a contacts surface 313 of body 312, an electric circuit is completed to ground (not shown) through piston 96a, providing a signal to the tool electronics (not shown) that formation probe assembly 50a has been fully retracted. After piston 96a makes contact with surface 313 of body 312, piston 96a continues to travel until making contact with base portion 105a of stem 92a. Heat shrink 320 is shrunk in place over wire 300 for mechanical protection.

Referring now to FIGS. 6A and 6B, formation probe assembly 50 is assembled such that piston base 118 is permitted to reciprocate along surface 113 of adapter sleeve 94, and piston outer surface 141 is permitted to reciprocate along surface 114. Similarly, snorkel base 125 is disposed within piston 96 and is adapted for reciprocal movement along surface 147 while flange 153 of scraper tube keeper 152 reciprocates along surface 145. Snorkel extension 126 is adapted for reciprocal movement along piston surface 120. Central passageway 127 of snorkel 98 is axially aligned with tubular extension 107 of stem 92, scraper tube keeper 152, scraper tube 150, scraper 160 and with screen 100. Formation probe assembly 50 is reciprocal between a fully retracted position, as shown in FIG. 6A, and a fully extended position, as shown in FIG. 6B. Also, scraper tube 150 is reciprocal between a fully retracted position, as shown in FIGS. 6A-6B, and a fully extended position, as is illustrated by a similar scraper tube 278 in FIGS. 7A-7E. When scraper tube 150 is fully retracted, fluid may be communicated between central passageway 108 of extension 107, passageway 155 of scraper tube keeper 152, passageway 151 of scraper tube 150, scraper bore 164, scraper apertures 166, screen 100, and the surrounding environment 15.

With reference to FIGS. 6A and 6B, the operation of formation probe assembly 50 will now be described. Formation probe assembly 50 is normally in the retracted position. Formation probe assembly 50 remains retracted when not in use, such as when the drill string is rotating while drilling if formation probe assembly 50 is used for an MWD application, or when the wireline testing tool is being lowered into borehole 8 if formation probe assembly 50 is used for a wireline testing application. FIG. 6A shows formation probe assembly 50 in the fully retracted position, except that scraper tube 150 is shown in the retracted position, and scraper tube 150 is typically extended when formation probe assembly 50 is in this position, as shown in FIGS. 7A-7E. FIGS. 7A-7F will be referred to in describing the operation of formation probe assembly 50 because the structures of formation probe assembly 50 previously described are similar to corresponding parts of probe assembly 200 seen in FIGS. 7A-7F.

Formation probe assembly 50 typically begins in the retracted position, as shown in FIG. 6A. Upon an appropriate command to formation probe assembly 50, a force is applied to base portion 118 of piston 96, preferably by using hydraulic fluid. Piston 96 extends relative to the other portions of formation probe assembly 50 until retainer ring 159 engages flange 153 of scraper tube keeper 152. This position of piston 96 relative to snorkel assembly 98 can be seen in FIG. 7B. As hydraulic fluid continues to be pumped into hydraulic fluid reservoir 54, piston 96 and snorkel assembly 98 continue to move upward together. Base portion 118 slides along adapter sleeve surface 113 until base portion 118 comes into contact with shoulder 170. After such contact, formation probe assembly 50 will continue to pressurize reservoir 54 until reservoir 54 reaches a certain pressure $P_1$. Alternatively, if seal pad 180 comes into contact with a borehole wall before base portion 118 comes into contact with shoulder 170, formation probe assembly 50 will continue to apply pressure to seal pad 180 by pressurizing reservoir 54 up to the pressure $P_1$. The pressure $P_1$ applied to formation probe assembly 50, for example, may be 1,200 p.s.i.

The continued force from the hydraulic fluid in reservoir 54 causes snorkel assembly 98 to extend such that the outer end of snorkel extension 126, inlet end 131 of screen 100 and the top of scraper 160 extend beyond seal pad surface 183 through seal pad aperture 186. This snorkel extending force must overcome the retract force being applied on the retract side of snorkel base portion 125 facing piston shoulder 172. Previously, the retract force, provided by retract accumulator 424 and the retract valves, was greater than the extend force, thereby maintaining snorkel 98 in the retract position. However, the extend force continues to increase until it overcomes the retract force at, for example, 900 p.s.i. Snorkel assembly 98 stops extending outward when snorkel base portion 125 comes into contact with shoulder 172 of piston 96. Scraper tube 150 and scraper 160 are still in the extended position, as is best shown with the snorkel assembly and piston configuration of FIG. 7E.

Alternatively, if snorkel assembly 98 comes into contact with a borehole wall before snorkel base portion 125 comes into contact with shoulder 172 of piston 96, continued force from the hydraulic fluid pressure in reservoir 54 is applied up to the previously mentioned maximum pressure. The maximum pressure applied to snorkel assembly 98, for example, may be 1,200 p.s.i. Preferably, the snorkel and seal pad will contact the borehole wall before either piston 96 or snorkel 98 shoulders at full extension. Then, the force applied on the seal pad is reacted by stabilizer 36, or other similar device disposed on or near probe collar 12.

If, for example, seal pad 180 had made contact with the borehole wall 16 before being fully extended and pressurized, then seal pad 180 should seal against the mudcake on borehole wall 16 through a combination of pressure and seal pad extrusion. The seal separates snorkel assembly 98 from the mudcake, drilling fluids and other contaminants outside of seal pad 180. As the snorkel assembly extends, snorkel extension 126, screen inlet end 131 and the top of scraper 160 pierce the mudcake that has been sealed off, and preferably go through the entire mudcake layer and into formation 9.

Figure 7A:
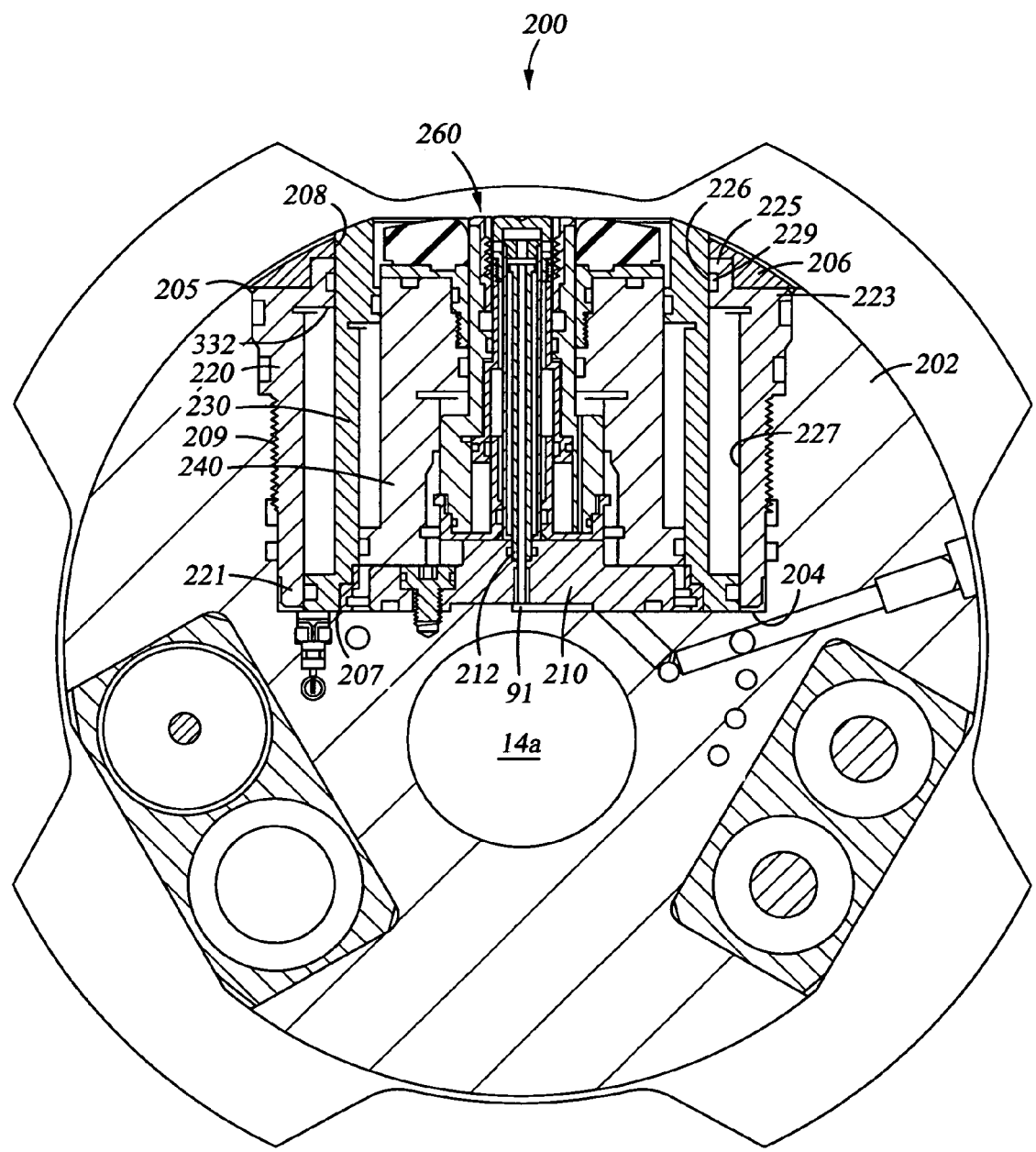
FIGS. 7A-7F are cross-sectional views of another embodiment of the formation probe assembly taken along the same line as seen in FIG. 6B, the probe assembly being shown in a different position in each of FIGS. 7A-7F.
Figure 7B:
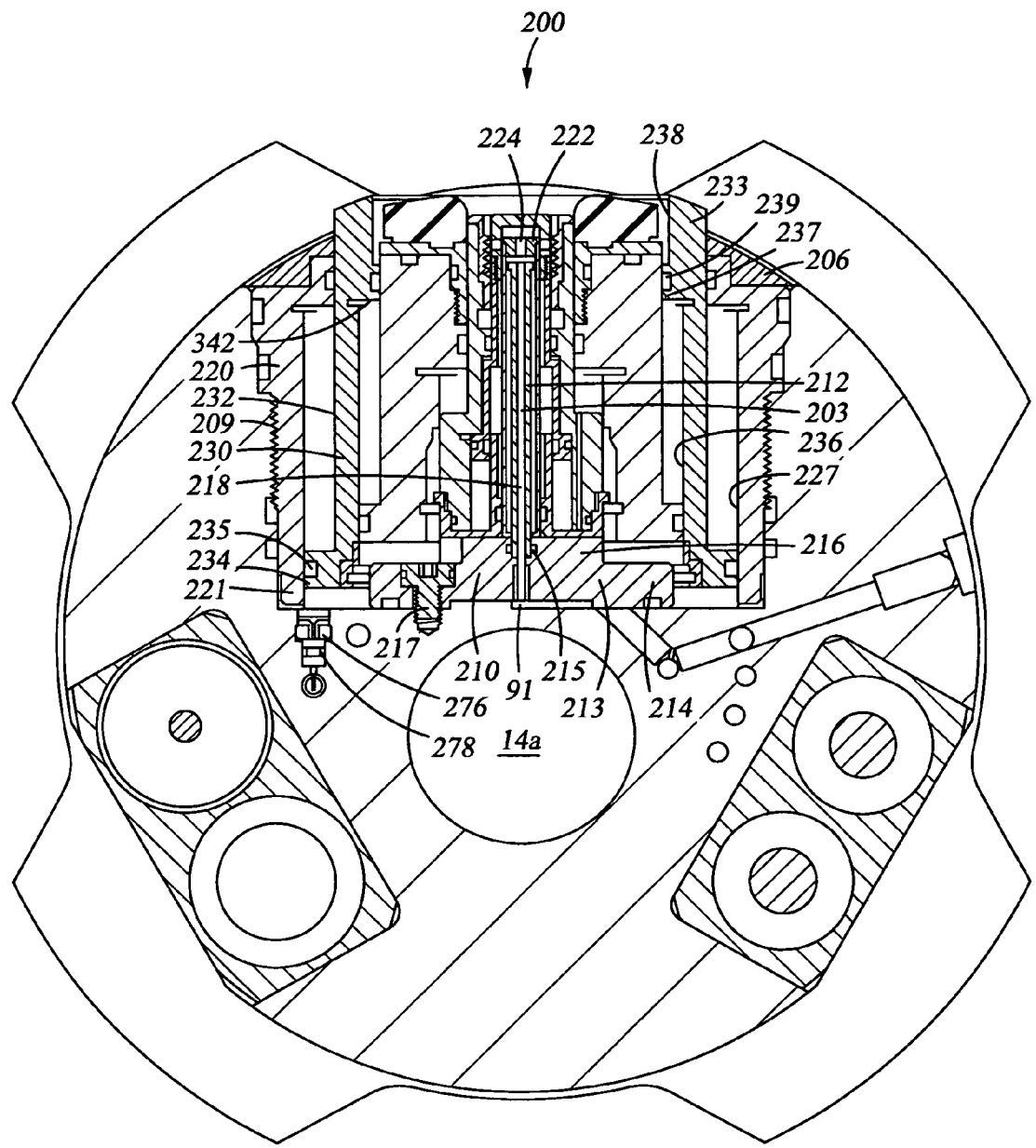
Figure 7C:
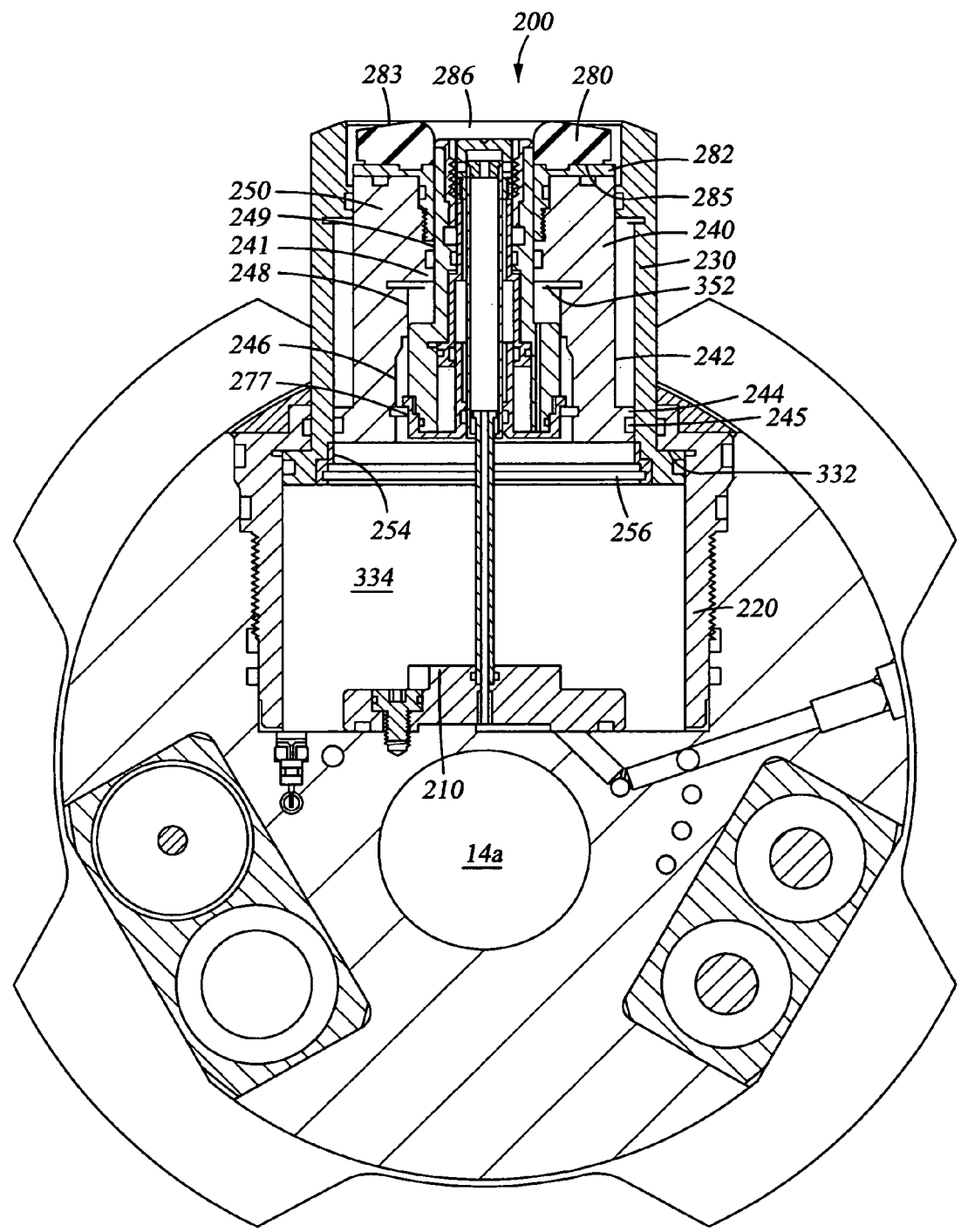
Figure 7D:
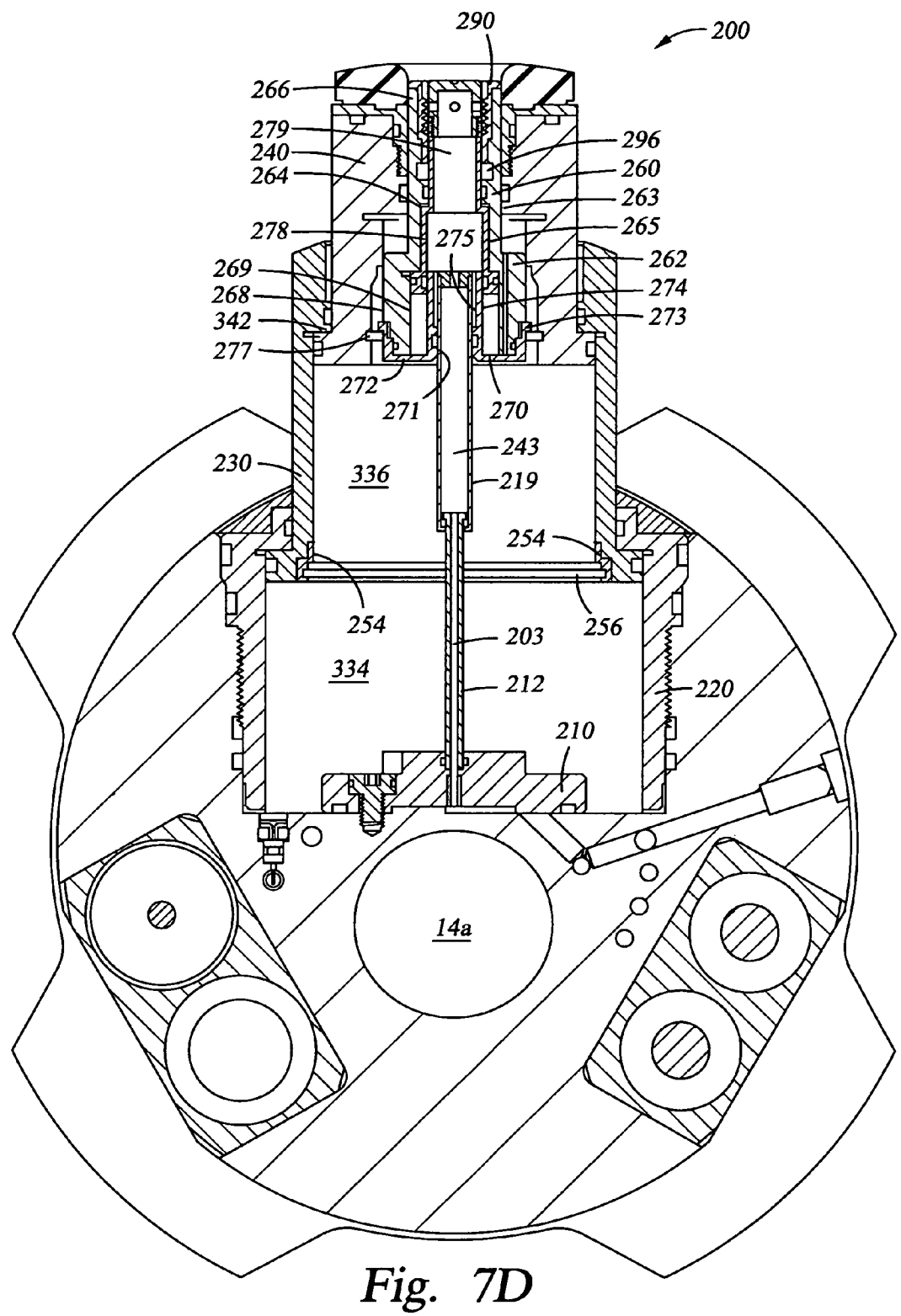
Figure 7E:
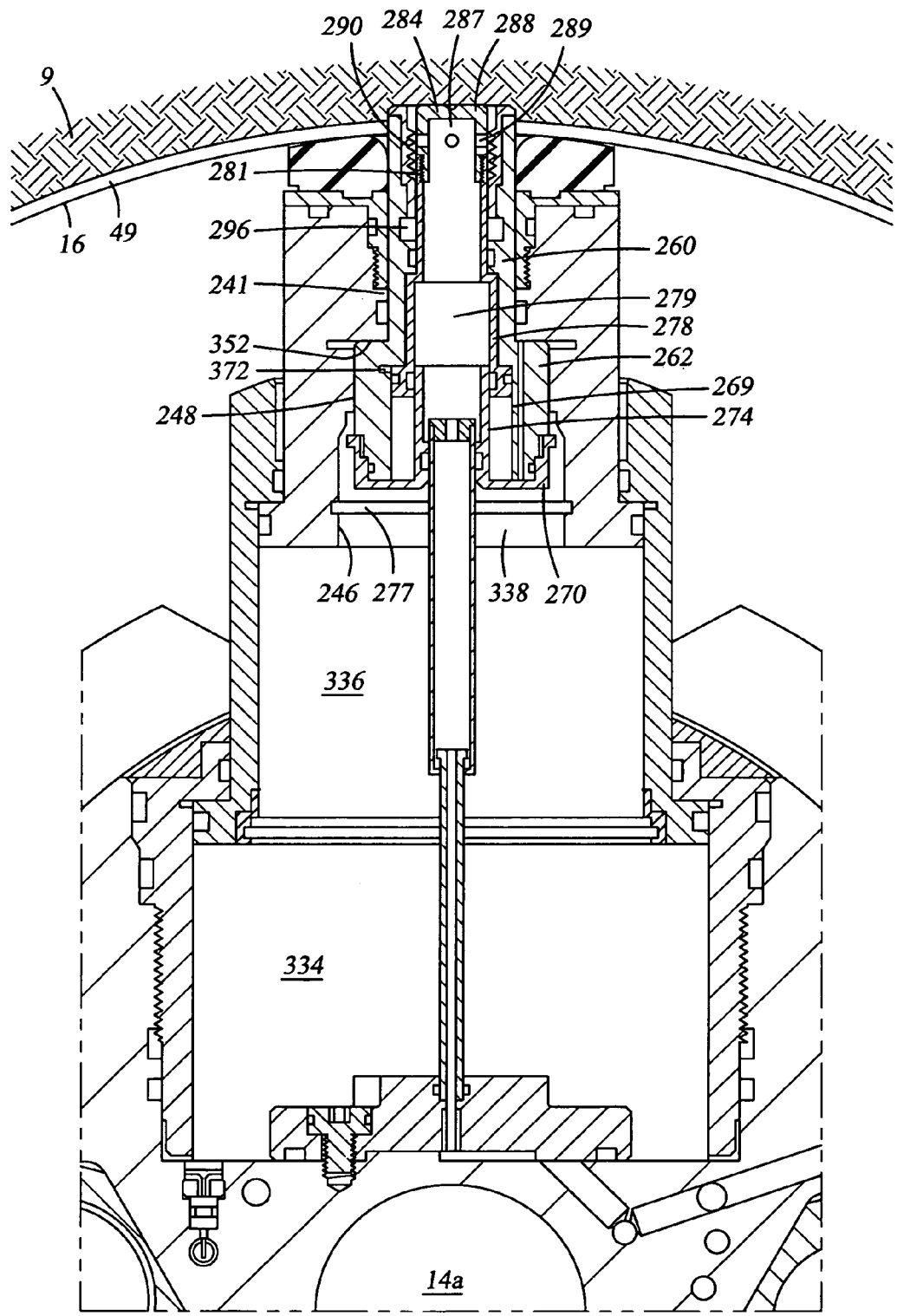

With screen 100 and scraper 160 extended, the piston 96 and snorkel 98 assembly configuration looks similar to the piston and snorkel configuration shown in FIG. 7E. While extending snorkel extension 126 into the mudcake and formation, contaminants and debris tend to gather on screen 100 which can affect the sampling of formation fluids. To clear the debris, which may be mudcake or other contaminants from previous sampling procedures, scraper 160 may be retracted after snorkel assembly 98 has been extended. A downward retract force is applied to scraper tube 150, preferably by applying a hydraulic fluid force downward on flange 177 of scraper tube 150. The cavity formed by scraper tube 150 and snorkel surface 124 fills with hydraulic fluid as scraper tube 150 moves downward, until scraper tube 150 bottoms out on scraper tube keeper 152. As scraper 160 is drawn within snorkel extension 126 during this process, scraper 160 passes through screen 100 while also frictionally engaging screen 100, thereby agitating and removing debris that has gathered on screen 100. Alternatively, as previously described, debris agitation may be achieved with rotational movement of scraper 160 about its longitudinal axis within screen 100. When scraper tube 150 is fully retracted, apertures 166 radially align with outlet end 135 of screen 100 such that fluid communication is possible between bore 132 of screen 100 and passageway 151 of scraper tube 150. This scraper 160 action that removes debris is preferably performed as part of the formation probe assembly 50 retract sequence, as described below.

To retract formation probe assembly 50, forces, or pressure differentials, may be applied to snorkel 98 and piston 96 in opposite directions relative to the extending forces. Simultaneously, the extending forces may be reduced or ceased to aid in probe retraction. A hydraulic force is applied to snorkel base portion 125 at shoulder 172 to push snorkel assembly 98 down until flange 153 of scraper tube keeper 152 sits on retainer ring 159, thereby fully retracting snorkel assembly 98. Concurrently, a hydraulic force is applied downward on piston base portion 118 at shoulder 170 until base portion 118 bottoms out on stem base portion 105, thereby fully retracting formation probe assembly 50. When piston 96 contacts stem base portion 105, probe retract switch 176 is triggered as described above, signaling a successful retraction of formation probe assembly 50. Scraper 160 may be extended to its original position at any time during retraction. When the extend pressure on the probe assembly, which provides the retract pressure for the scraper assembly because the probe assembly extend portions are hydraulically coupled to the scraper assembly retract portions, falls below the extend pressure on the scraper assembly, scraper 160 is extended.

Another embodiment of the present invention is shown in FIGS. 7A-7F. Probe collar 202 having flowbore 14a houses telescoping formation probe assembly 200. Probe assembly 200, as compared to formation probe assembly 50, extends to reach a borehole wall that is further displaced from collar 202. Such borehole walls that may be displaced further from collar 12 may be found in washed out portions of a well, irregular holes in the well, wells drilled with hole openers or near bit reamers or large wells drilled with bi-center bits. Telescoping probe assembly 200 is useful in reaching a borehole wall in these types of wells.

Telescoping probe assembly 200 generally includes stem plate 210, stem 212, a generally cylindrical threaded adapter sleeve 220, an outer piston 230 adapted to reciprocate within adapter sleeve 220, a piston 240 adapted to reciprocate within outer piston 230, and a snorkel assembly 260 adapted for reciprocal movement within piston 240. Probe collar 202 includes an aperture 204 for receiving telescoping formation probe assembly 200. Cover plate 206 fits over the top of probe assembly 200 and retains and protects assembly 200 within probe collar 202. Formation probe assembly 200 is configured to extend through aperture 208 in cover plate 206.

Referring first to FIG. 7A, adapter sleeve 220 includes inner end 221 near the bottom 207 of aperture 204. Adapter sleeve 220 is secured within aperture 204 by threaded engagement with collar 202 at segment 209. The outer end 223 of adapter sleeve 220 extends to be substantially flushed with opening 205 of aperture 204 formed in collar 202. Outer end 223 includes flanges 225 for engaging cover plate 206. Adapter sleeve 220 includes cylindrical inner surface 227 having reduced diameter portion 226. A seal 229 is disposed in surface 226.

Referring next to FIG. 7B, stem plate 210 includes a circular base portion 213 with an outer flange 214. Extending from base 213 is a short extension 216. Extending through extension 216 and base 213 is a central passageway 218 for receiving the lower end 215 of stem 212 having central passageway 203. Lower end 215 threadedly engages stem plate passageway 218. Central passageway 218 is in fluid connection with fluid passageway 91 (not shown, but seen schematically in FIG. 9) that connects to fluid passageway 93 (not shown, but seen schematically in FIG. 9) leading to other portions of tool 10, including equalizer valve 60. Stem 212 extends up through the center of probe assembly 200. Disposed about stem 212 is outer stem 219. Threadedly engaged at the top of outer stem 219 is outer stem capture screw 222 having central bore 224.

Referring again to FIG. 7B, outer piston 230 is slidingly retained within adapter sleeve 220 and generally includes cylindrical outer surface 232 having an increased diameter base portion 234. A seal 235 is disposed in increased diameter portion 234. Outer piston 230 also includes cylindrical inner surface 236 having reduced diameter portions 237, 238 at upper extending portion 233. A seal 239 is disposed in surface 237.

Referring now to FIG. 7C, piston 240 is slidingly retained within outer piston 230 and generally includes cylindrical outer surface 242 having an increased diameter base portion 244. A seal 245 is disposed in increased diameter portion 244. Just below base portion 244, piston 240 rests on capture sleeve 254 which is engaged with base portion 234 of outer piston 230. Retainer ring 256 is engaged at the bottom of capture sleeve 254 and holds the capture sleeve in position. Piston 240 also includes cylindrical inner surface 246 having reduced diameter portion 248. Piston 240 further includes central bore 249 having bore surface 241 and extending through upper extending portion 250.

At the top of extending portion 250 of piston 240 is a seal pad 280. As shown in FIGS. 7A-7F, seal pad 280 may be donut-shaped with a curved outer surface 283 and central aperture 286. However, seal pad 280 may include numerous other geometries as is known in the art, or, for example, as is seen in U.S. patent application Ser. No. 10/440,835 entitled "MWD Formation Tester." Base surface 285 of seal pad 280 may be coupled to a skirt 282. Seal pad 280 may be bonded to skirt 282, or otherwise coupled to skirt 282, such as by molding seal pad 280 onto skirt 282 such that the seal pad material fills grooves or holes in skirt 282, as can be seen in U.S. patent application Ser. No. 10/440,835. Skirt 282 is detachably coupled to extending portion 250 by way of threaded engagement with surface 241 of central bore 249, or other means of engagement, such as a pressure fit with central bore surface 241. Because the seal pad/skirt combination is detachable from extending portion 250, it is easily replaced in the field. Alternatively, seal pad 280 may be coupled directly to extending portion 250 without using a skirt. Other characteristics of seal pad 280, such as seal pad material and the way seal pad 280 functions, are similar to the previously described seal pad 180.

Referring now to FIG. 7D, snorkel 260 includes a base portion 262, a snorkel extension 266, and a central passageway 264 extending through base 262 and extension 266. Base portion 262 includes a cylindrical outer surface 268 and inner surface 269. Extension 266 includes a cylindrical outer surface 263 and inner surface 265. Disposed inside the top of extension 266 is a screen 290, best shown in FIG. 7F. Screen 290 is a generally tubular member having a central bore 292 extending between a fluid inlet end 294 and fluid outlet end 296. Screen 290 further includes a flange 298 adjacent to fluid inlet end 294 and an internally slotted segment 293 having slots 295. Between slotted segment 293 and outlet end 296, screen 290 includes threaded segment 297 for threadedly engaging snorkel extension 266.

Figure 7F:
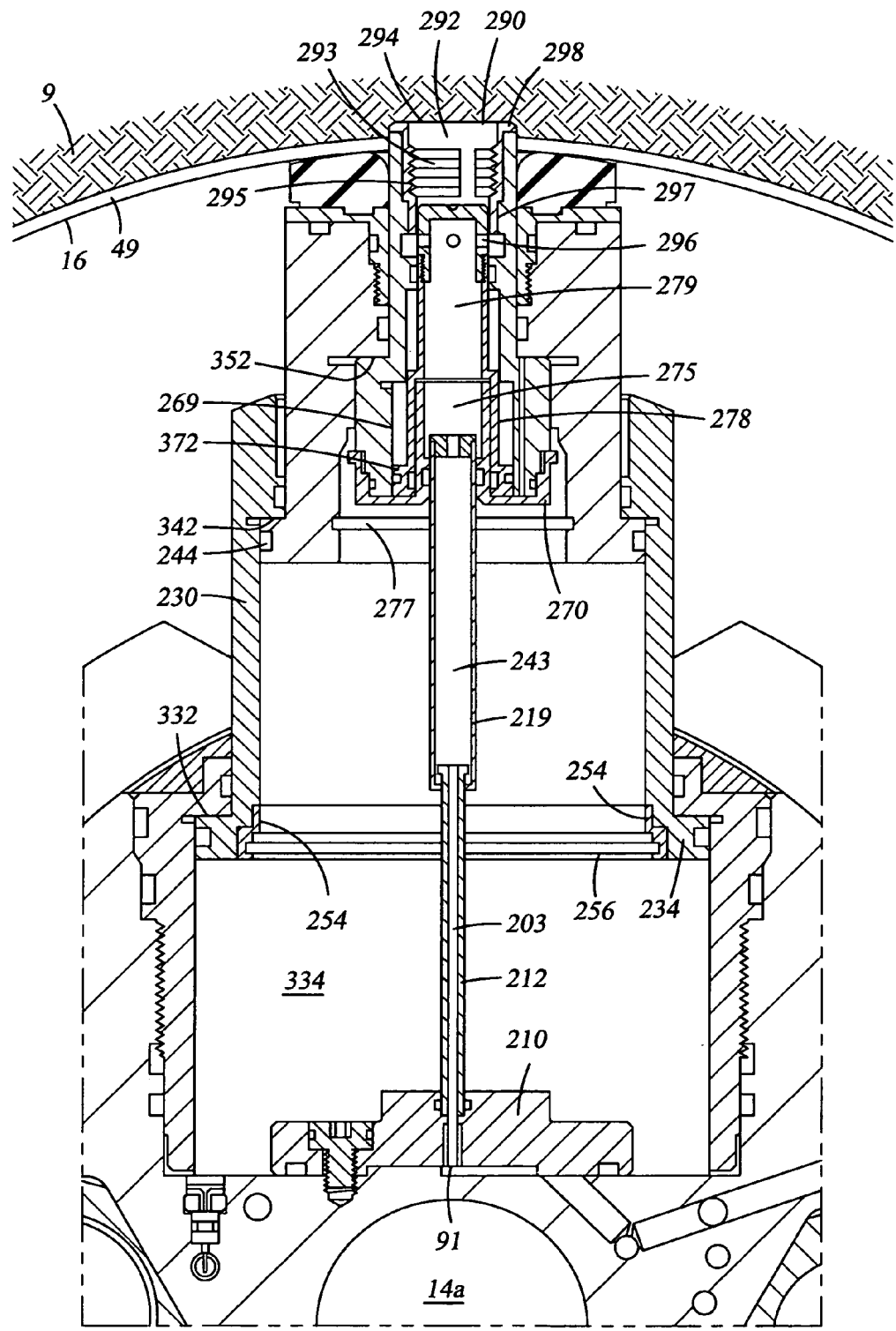

Threaded to the bottom of base portion 262 of snorkel 260 is scraper tube keeper 270 having a circular base portion 272 and retaining edge 273, a tubular extension 274 having a central passageway 275 and a central aperture 271 for receiving outer stem 219. Outer stem 219 includes central passageway 243. A retainer ring 277 is radially aligned and engageable with retaining edge 273, which limits the movement of snorkel 260 in the retract direction. After snorkel 260 has been extended, retainer ring 277 is disposed below scraper tube keeper 270 in piston surface 246, as can be seen in FIG. 7E. Scraper tube keeper 270 supports scraper tube 278 when scraper tube 278 is in the retracted position shown in FIG. 7F, and isolates the hydraulic fluid reservoir formed by tubular extension 274 and snorkel surface 269. Scraper tube 278 having central passageway 279 is slidingly retained above scraper tube keeper 270 in passageway 264 of snorkel 260. Coupled at the top of scraper tube 278 is scraper 288. Scraper 288 is threadedly engaged with scraper tube 278 at threaded segment 281. Scraper 288 is a generally cylindrical member including scraper plug portion 284, central bore 287 and apertures 289 that are in fluid communication with central bore 287. Scraper 288 is disposed within central bore 292 of screen 290 and is reciprocal between screen inlet end 294 and outlet end 296; alternatively, as previously described, scraper 288 may be rotatable within screen 290. When scraper tube 278 and scraper 288 are in their retracted positions, as shown in FIG. 7F, apertures 289 are in fluid communication with fluid outlet end 296 of screen 290, thereby allowing fluid to pass from screen 290, through scraper bore 287, and into central passageway 279 of scraper tube 278.

Referring back to FIG. 7B, a probe retract switch connector 276 is disposed in aperture 278 of probe collar 202, just beneath inner end 221 of sleeve 220. The details of switch connector 276 are similar to the previously described switch 176, above, with reference to FIGS. 8A-8B. Although not shown, switch and connector 276 are electrically coupled to a contact assembly disposed in stem base portion 213. The contact assembly contacts piston 240 when piston 240 is bottomed out on stem base portion 213 indicating to the tool electronics that probe assembly 200 is fully retracted.

Formation probe assembly 200 is assembled such that outer piston base 234 is permitted to reciprocate along surface 227 of adapter sleeve 220, and outer piston surface 232 is permitted to reciprocate along surface 226. Similarly, piston base portion 244 is permitted to reciprocate along outer piston inner surface 236, and piston surface 242 is permitted to reciprocate along outer piston surface 237. Snorkel base portion 262 is disposed within piston 240 and is adapted for reciprocal movement along surface 248 while retaining edge 273 of scraper tube keeper 270 reciprocates between retainer ring 277 and decreased diameter portion 248. Snorkel extension 266 is adapted for reciprocal movement along piston surface 241. Central passageway 264 of snorkel 260 is axially aligned with stem 212, outer stem 219, scraper tube keeper 270, scraper tube 278, scraper 288 and with screen 290. Formation probe assembly 200 is reciprocal between a fully retracted position, as shown in FIG. 7A, and a fully extended position, as shown in FIG. 7F. Also, scraper tube 278 is reciprocal between a fully extended position, as shown in FIGS. 7A-7E, and a fully retracted position, as is illustrated in FIG. 7F. When scraper tube 278 is fully retracted, fluid may be communicated between central passageway 203 of stem 212, passageway 243 of outer stem 219, passageway 275 of scraper tube keeper 270, passageway 279 of scraper tube 278, bore 287 of scraper 288, scraper apertures 289, screen 290, and the surrounding environment 15.

With reference to FIGS. 7A-7F, the operation of formation probe assembly 200 will now be described. Formation probe assembly 200 typically begins in the retracted position, as shown in FIG. 7A. Assembly 200 remains retracted when not in use, such as when the drill string is rotating while drilling if assembly 200 is used for an MWD application, or when the wireline testing tool is being lowered into borehole 8 if assembly 200 is used for a wireline testing application. FIG. 7A shows assembly 200 in the fully retracted position, with scraper tube 278 in the extended position.

Upon an appropriate command to probe assembly 200, a force is applied to base portion 234 of outer piston 230, preferably by using hydraulic fluid. Outer piston 230 raises relative to adapter sleeve 220, with outer piston base portion sliding along sleeve surface 227. Retainer ring 256 and capture sleeve 254 force piston 240 upward along with outer piston 230 by pressing on piston base portion 244. As seen in FIG. 7B, snorkel 260 remains seated on stem plate 210 while outer piston 230 and piston 240 begin to rise, until retainer ring 277 contacts retaining edge 273 of scraper tube keeper 270. At this point, the upward hydraulic force continues to be applied to the reciprocal parts of assembly 200, and fluid reservoir 334 enlarges and fills until outer piston base portion 234 seats on adapter sleeve shoulder 332, as shown in FIG. 7C. Then hydraulic fluid is directed into reservoir 336, causing piston 240 and snorkel 260 to extend out, with piston base portion 244 sliding along outer piston surface 236. Finally, piston base portion 244 seats on outer piston shoulder 342, as shown in FIG. 7D. Once again, typically, snorkel 260 and seal pad 280 (FIG. 7C) contact the borehole wall prior to reaching full extension, as previously described. The tool stabilizer, or other such device, will react the probe extension force.

Before reaching the position shown in FIG. 7D, seal pad 280 is preferably engaged with the borehole wall (not shown). To form a seal with seal pad 280, probe assembly 200 will continue to pressurize the reservoirs 334, 336 until the reservoirs reach a maximum pressure. Alternatively, if seal pad 180 comes into contact with the borehole wall before probe assembly 200 is fully extended, probe assembly 200 will continue to apply pressure to seal pad 280 up to the previously mentioned maximum pressure. The maximum pressure applied by probe assembly 200, for example, may be 1,200 p.s.i.

As hydraulic fluid continues to be pumped through reservoirs 334, 336, snorkel 260 slides along surfaces 248, 241 as hydraulic fluid is directed into reservoir 338 and this snorkel extend force increases. This snorkel extending force must overcome the retract force being applied on the retract side of snorkel base portion 262 facing piston shoulder 352. Previously, the retract force, provided by retract accumulator 424 and the retract valves, was greater than the extend force, thereby maintaining snorkel 260 in the retract position. However, the extend force continues to increase until it overcomes the retract force at, for example, 900 p.s.i. Snorkel base portion 262 finally seats on piston shoulder 352, as shown in FIG. 7E. Snorkel 260 has extended such that the outer end of snorkel extension 266, inlet end 294 of screen 290 and the top of scraper 288 extend beyond seal pad surface 283 through seal pad aperture 286. Scraper tube 278 and scraper 288 are still in the extended position, as seen in FIG. 7E. If seal pad 280 is engaged with the borehole wall, snorkel extension 266, screen inlet end 294 and the top of scraper 288 pierce the mudcake that has been sealed off, and preferably go through the entire mudcake layer and into formation 9.

As previously described, extending snorkel extension 266 into the mudcake and formation causes contaminants and debris to gather on screen 290, which can affect the sampling of formation fluids. Floating scraper 288 is used to clear the debris in a similar fashion to that described with respect to formation probe assembly 50. A downward force is applied to scraper tube 278, preferably by applying a hydraulic fluid force downward on flange 372 of scraper tube 278. The cavity formed by scraper tube 278 and inner snorkel surface 269 fills with hydraulic fluid as scraper tube 278 moves downward, until tube flange 372 seats on scraper tube keeper 270. As scraper 288 is drawn within snorkel extension 266 during this process, scraper 288 passes through screen 290, agitating and removing debris that has gathered on screen 290 through frictional engagement between scraper 288 and screen 290, as previously described. Also previously described was an alternative embodiment including a rotating screen 290, equally applicable here. When scraper tube 278 is fully retracted, apertures 289 radially align with screen outlet end 296 such that fluid communication is possible between screen bore 292 and passageway 279 of scraper tube 278. This scraper 288 action that removes debris is preferably performed as part of the formation probe assembly 200 retract sequence, as described below.

To retract probe assembly 200, forces, or pressure differentials, may be applied to probe assembly 200 in opposite directions relative to the extending forces. Simultaneously, the extending forces may be reduced or ceased to aid in probe retraction. First, and preferably, a pressure differential is applied across flange 372 of scraper tube 278 by increasing the hydraulic fluid pressure on the bottom of flange 372. This extends scraper tube 278 until scraper 288 is fully extended once again, wiping screen 290 clean as scraper 288 passes through it. Next, a hydraulic force is applied to snorkel base portion 262 at shoulder 352 to push snorkel assembly 260 down until retaining edge 273 of scraper tube keeper 270 sits on retainer ring 277, thereby fully retracting snorkel assembly 260. Next, a hydraulic force is applied downward on piston base portion 244 at shoulder 342 until base portion 244 seats on capture sleeve 254 and retainer ring 256 adjacent outer piston base portion 234. From this position, a hydraulic fluid is inserted at adapter sleeve shoulder 332 onto outer piston base portion 234 to force outer piston 230 downward. Outer piston 230 then seats on bottom 207 of aperture 204, and the piston 240/snorkel 260 assembly seats on stem plate 210, thereby fully retracting probe assembly 200. When piston 240 contacts stem plate 210, probe retract switch 276 is triggered as described above, signaling a successful retraction of assembly 200.

It is noted that formation probe assembly 50 may only extend the outer end of piston extending portion 119 past the outer end of sleeve 94 a distance that is less than the length of piston 96. The length of piston 96 is defined as the distance between the uppermost end of extending portion 119 and the lowermost end of base portion 118. In comparison, probe assembly 200 may extend the outer end of piston upper portion 250 past the outer end of sleeve 220 a distance that exceeds the length of piston 240. Therefore, the telescoping feature of probe assembly 200, i.e., the concentric pistons 230, 240, allows seal pad 280 to engage a borehole wall that is significantly further from collar 202 than the length of piston 240.

Figure 14:
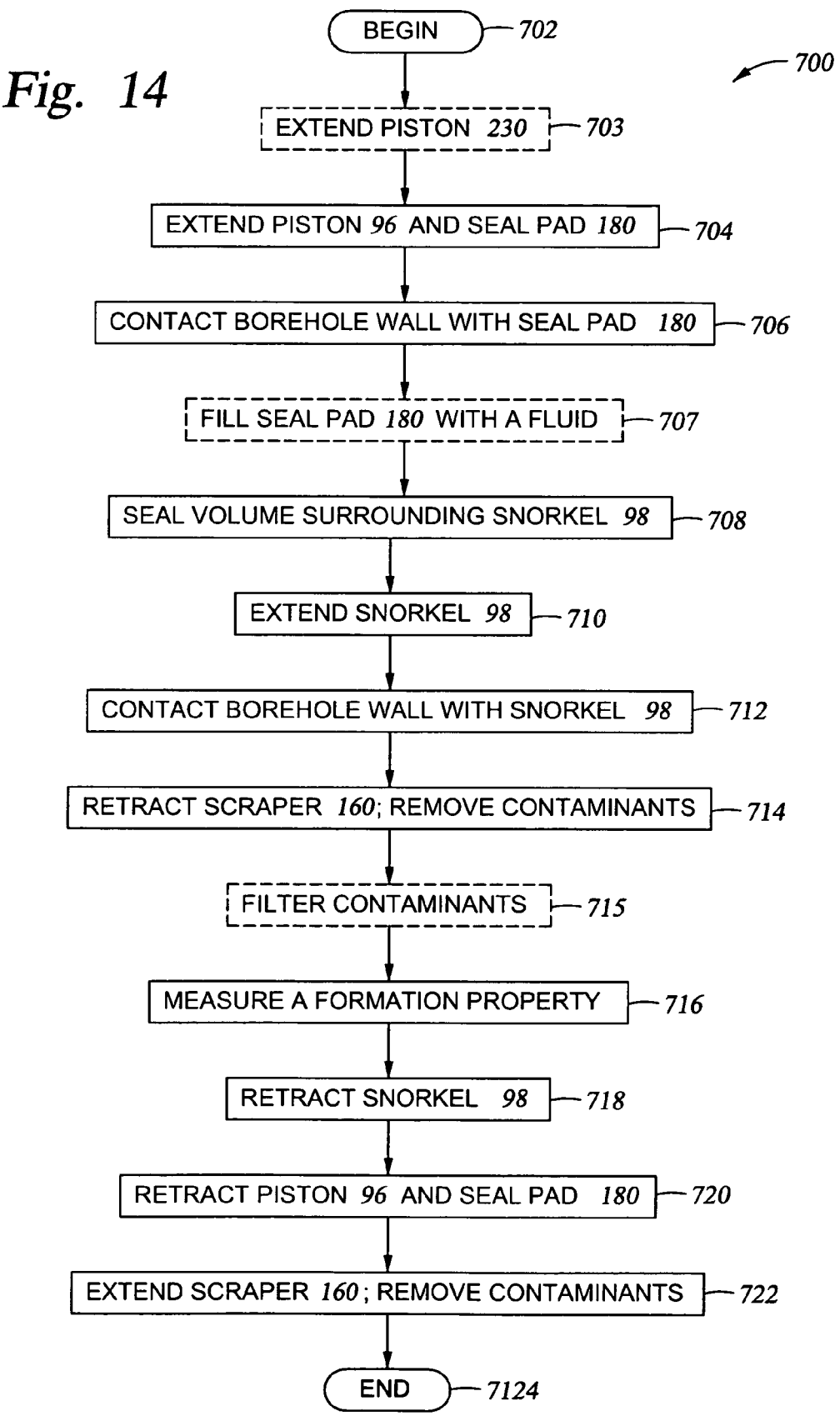
FIG. 14 is a flow diagram of a formation test sequence.

Referring now to FIG. 14, an example of how the probe assemblies may be used to test a formation will be described. The test sequence 700 may begin (box 702) upon a command to the tool 10 from the surface of the borehole, for example, or from embedded tool software. In a first embodiment, piston 96 and seal pad 180 may be extended (box 704). In a further embodiment, piston 230 may be extended (box 703) to provide the telescopic effect previously described. The borehole wall is contacted by seal pad 180 (box 706). Next, a volume surrounding snorkel 98 is sealed (box 708). In a further embodiment, seal pad 180 may be filled with a fluid (box 707), as previously described. Continuing with the sequence 700, snorkel 98 may be extended (box 710), and the borehole wall contacted by snorkel 98 (box 712). Scraper 160 may now be retracted (box 714), causing agitation and removal of contaminants from snorkel 98. A formation property may then be measured (box 716). In a further embodiment, contaminants may be filtered (box 715), such as by a screen 100. After measuring a formation property, snorkel 98 is retracted (box 718), piston 96 and seal pad 180 are retracted (box 720), and scraper 160 is extended (box 722). The extension of scraper 160 may also serve to remove contaminants from snorkel 98. Sequence 700 ends (box 724) with a formation property having been measured for uses further described herein.

In an alternative embodiment of tool 10, formation probe assemblies 50, 200 may be located elsewhere in the tool. Referring now to FIG. 3B, formation probe assembly 50 may instead be disposed in blade 37 of stabilizer 36. Equalizer valve 60, shutoff valve 74 and draw down pistons 70, 72 may remain in the same position as shown in FIG. 3B, although it is preferred that they be in closer proximity to formation probe assembly 50, and therefore may be moved closer to stabilizer 36. Locating formation probe assemblies 50, 200 in stabilizer blade 37 allows the assemblies to be placed closer to the borehole wall while still mounted in a robust portion of the tool. Further, the other blades of stabilizer 36 may be used to back up formation probe assemblies 50, 200 as they extend out and pressure up against the borehole wall.

Even if formation probe assemblies 50, 200 are not disposed in stabilizer 36, the blades of stabilizer 36 are preferably used to back up the extending formation probe assemblies 50, 200. To provide a sufficient sealing force for the probe seal pad, a reactive force must be applied to the tool to counter the force of the extending probe. Alternatively, if a stabilizer is not used, centralizing pistons such as those illustrated and described in U.S. patent application Ser. No. 10/440,593, filed May 19, 2003 and entitled "Method and Apparatus for MWD Formation Testing," hereby incorporated by reference for all purposes, may be used.

With respect to any of the probe assembly embodiments described above, a probe assembly position indicator may be included in the probe assembly to measure the distance that the probe assembly has extended from its fully retracted position. Numerous sensors may be used to detect the position of the probe assembly as it extends. In one embodiment, the probe assembly position indicator may be a measure of the volume of hydraulic fluid used to extend the probe assembly. If the probe assembly is configured to use hydraulic fluid and pressure differentials to extend, as is described in the embodiments above, the volume of fluid pumped into the probe assembly may be measured. With known diameters for the adapter sleeves and pistons, the distance that the pistons have extended may be calculated using the volume of fluid that has been pumped into the probe assembly. To make this measurement more accurate, certain characteristics of the probe assembly may be accounted for, such as seal pad compression as it compresses against the borehole wall.

In another embodiment of the probe assembly position indicator, an optical or acoustic sensor may be disposed in the probe assembly, such as in an aperture formed in the piston surface 141 of formation probe assembly 50, or piston surface 242 of probe assembly 200. The optical or acoustic sensor may measure the distance the piston moves from a known reference point, such as the piston position when the probe assembly is fully retracted. Such devices are well known to one skilled in the art.

In yet another embodiment, a potentiometer, resistance-measuring device or other such device well known to one skilled in the art may be used to detect movement of the reciprocating portions of the probe assemblies through electrical means. The potentiometer or resistance-measuring device may measure voltage or resistance, and such information can be used to calculate distance.

The distance measurement gathered from the probe position indicator may be used for numerous purposes. For example, the borehole caliper may be calculated using this measurement, thereby obtaining an accurate measurement of the borehole diameter. Alternatively, multiple probes may be spaced radially around the drill string or wireline instrument, and measurements may be taken with the multiple probes to obtain borehole diameter and shape. Having an accurate borehole caliper measurement allows the driller to know where borehole breakout or collapse may be occurring. The caliper measurement may also be used to help correct formation evaluation sensors. For example, resistivity measurements are affected by borehole size. Neutron corrections applied to a neutron tool are also affected, as well as density corrections applied to a density tool. Other sensor tools may also be affected. An accurate borehole caliper measurement assists in correcting these tools, as well as any other drilling, production and completion process that requires borehole size characteristics, such as cementing.

Figure 9:
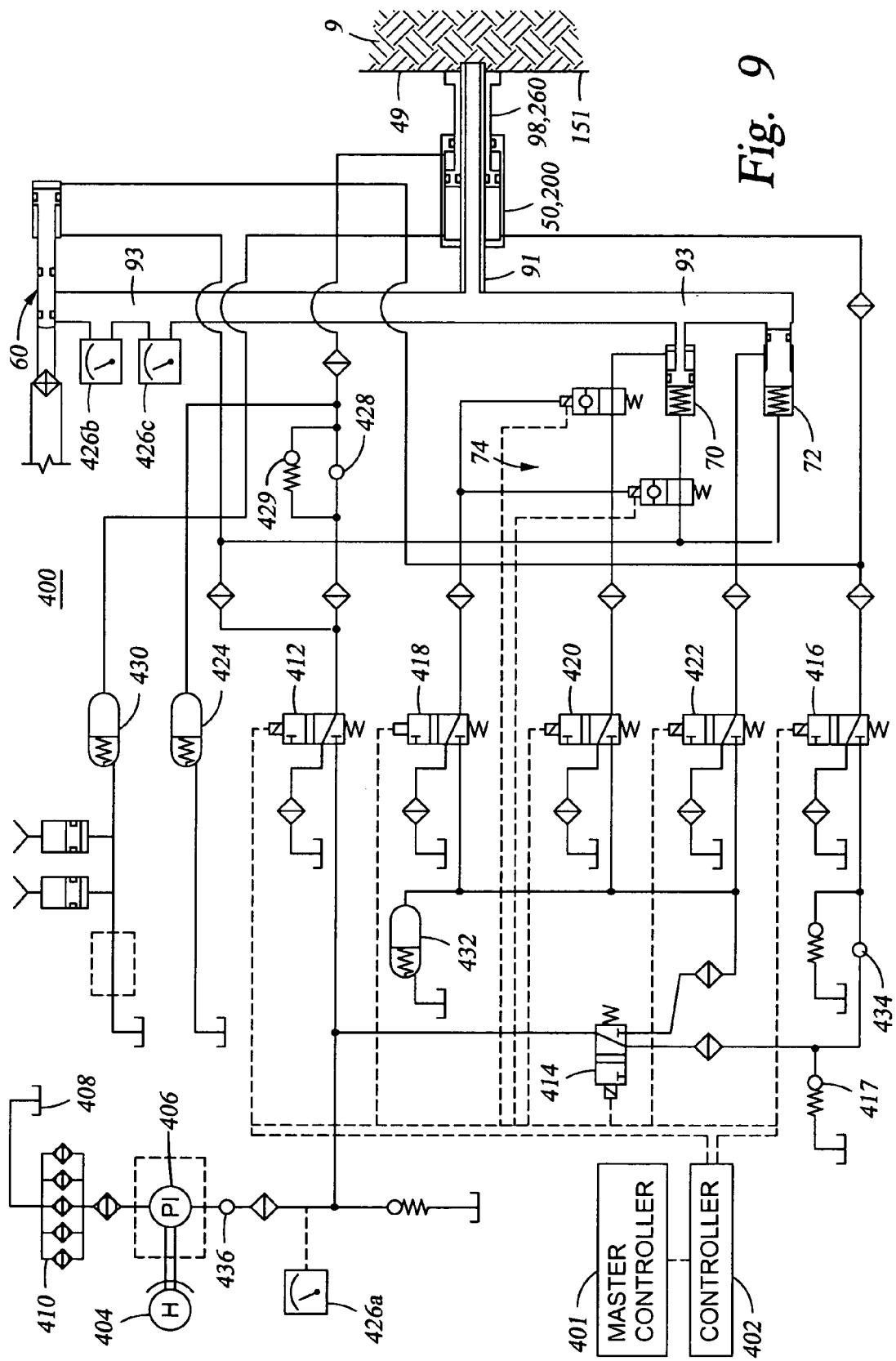
FIG. 9 is a schematic view of a hydraulic circuit employed in actuating the formation tester apparatus.

In another embodiment, the probe position indicator may be used to correct for probe flow line volume changes. Flow lines, such as flow lines 91, 93 in FIGS. 6A, 6B and 9, are susceptible to volume changes as the probe seal pad compresses and decompresses. Particularly, when the seal pad is engaged with the borehole wall and a formation test is in progress, the pressure from drawing down the formation fluids causes the seal pad to compress and the flow line volume to increase. The flow line volume is used in several formation calculations, such as mobility; permeability may then be calculated using formation fluid viscosity and density. To correct for this volume change and obtain an accurate flow line volume measurement, probe positioning may be used. Further, although the full flow line volume is known, if the probe does not fully extend before engaging the borehole wall, only a portion of the flow line volume is used and that quantity may not be known. Therefore, the probe position may be used to correct for the portion of the flow line volume that is not being used.

The embodiments of the position indicator described above may also be applied to the draw down piston assemblies, described in more detail below, for knowing where in the cylinder the draw down piston is located, and how the piston is moving. Volume and diameter calculations may be used to obtain distance moved, or sensors may be used as described above. Thus, the exact distance the piston has moved may be obtained, rather than relying on the volume of fluid used to actuate the piston as an indication of distance moved. Further, the steadiness of the draw down may be obtained from the position indicator. The rate may be calculated from the distance measured, and the steadiness of the rate may be used to correct other measurements.

For example, to gain a better understanding of the formation's permeability or the bubble point of the formation fluids, a reference pressure may be chosen to draw down to, and then the distance the draw down piston moved before that reference pressure was reached may be measured by the draw down piston position indicator. If the bubble point is reached, the distance the piston moved may be recorded and sent to the surface, or to the software in the tool, so that the piston may be commanded to move less and thereby avoid the bubble point.

Sensors intended for other purposes may also be disposed in the probe assemblies. For example, a temperature sensor, known to one skilled in the art, may be disposed on the probe assembly for taking annulus or formation temperature. In one embodiment, the temperature sensor may be placed in the snorkel extensions 126, 266. In the probe assembly retracted position, the sensor would be adjacent the annulus environment, and the annulus temperature could be taken. In the probe assembly extended position, the sensor would be adjacent the formation, allowing for a formation temperature measurement. Such temperature measurements could be used for a variety of reasons, such as production or completion computations, or evaluation calculations such as permeability and resistivity. These sensors may also be placed adjacent the probe assemblies, such as in the stabilizer blades or centralizing pistons.

Figure 11:
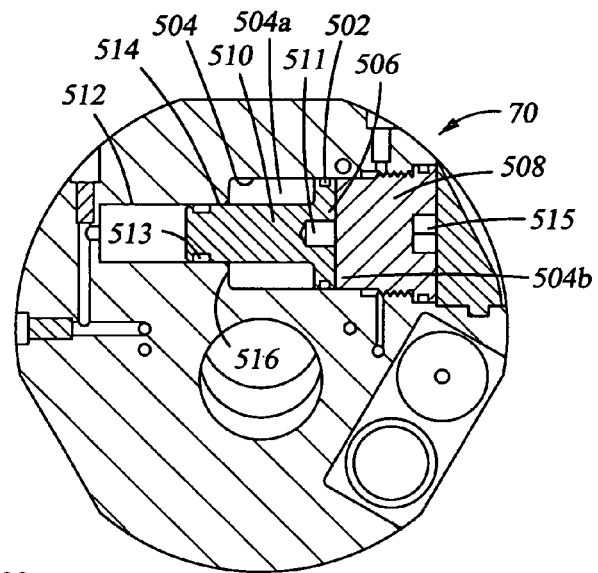
FIGS. 11-13 are elevation views, in cross-section, of the draw down piston and shutoff valve assemblies disposed in the probe collar of the formation tester assembly.

Referring back to FIGS. 3B and 5, it can be seen that probe collar 12 also houses draw down piston assemblies 70, 72 and draw down shutoff valve assembly 74. Referring now to FIG. 11, draw down piston assembly 70 generally includes annular seal 502, piston 506, plunger 510 and endcap 508. Piston 506 is slidingly received in cylinder 504 and plunger 510, which is integral with and extends from piston 506, is slidingly received in cylinder 514. In FIG. 11, piston 506 is in its drawn down position, but is typically biased to its uppermost or shouldered position at shoulder 516. A bias spring (not shown) biases piston 506 to the shouldered position, and is disposed in lower cylinder portion 504b between piston 506 and endcap 508. Separate hydraulic lines (not shown) interconnect with cylinder 504 above and below piston 506 in portions 504a, 504b to move piston 506 either up or down within cylinder 504 as described more fully below. Plunger 510 is slidingly disposed in cylinder 514 coaxial with cylinder 504. Cylinder 512 is the upper portion of cylinder 514 that is in fluid communication with the longitudinal passageway 93 (seen schematically in FIG. 9) that interconnects with draw down shutoff valve assembly 74, draw down piston 72, formation probe assembly 50, 200 and equalizer valve 60. Cylinder 512 is flooded with drilling fluid via its interconnection with passageway 93. Cylinder 514 is filled with hydraulic fluid beneath seal 513 via its interconnection with hydraulic circuit 400.

Endcap 508 houses a contact switch (not shown) having a contact that faces toward piston 506. A wire 515 is coupled to the contact switch. A plunger 511 is disposed in piston 506. When drawdown of piston assembly 70 is complete, as shown in FIG. 11, piston 506 actuates the contact switch by causing plunger 511 to engage the contact of the contact switch, which causes wire 515 to couple to system ground via the contact switch to plunger 511 to piston 506 to endcap 508 which is in communication with system ground (not shown).

Figure 12:
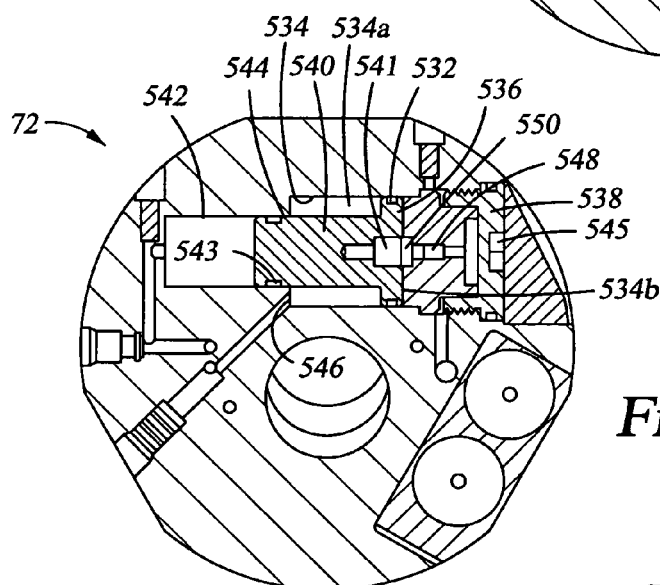
Figure 13:
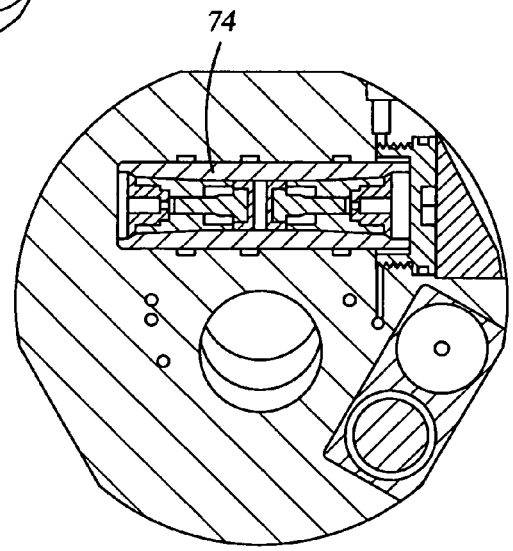

Referring to FIG. 12, a second draw down piston assembly 72 is shown. Draw down piston 72 is similar to piston 70, with the most notable difference being that the draw down volume is greater and the assembly does not include a bias spring. Draw down piston assembly 72 generally includes annular seal 532, piston 536, plunger 540 and endcap 538. Piston 536 is slidingly received in cylinder 534 and plunger 540, which is integral with and extends from piston 536, is slidingly received in cylinder 544. Plunger 540 and cylinder 544 have greater diameters than the corresponding portions of piston 70. In FIG. 12, piston 536 is in its drawn down position, but is typically maintained at its uppermost or shouldered position at shoulder 546 by hydraulic force. Separate hydraulic lines (not shown) interconnect with cylinder 534 above and below piston 536 in portions 534a, 534b to move piston 536 either up or down within cylinder 534 as described more fully below. Plunger 540 is slidingly disposed in cylinder 544 coaxial with cylinder 534. Cylinder 542 is the upper portion of cylinder 544 that is in fluid communication with the longitudinal passageway 93 (seen schematically in FIG. 9) that interconnects with draw down shutoff valve assembly 74, draw down piston 70, formation probe assembly 50, 200 and equalizer valve 60. Cylinder 542 is flooded with drilling fluid via its interconnection with passageway 93. Cylinder 544 is filled with hydraulic fluid beneath seal 543 via its interconnection with hydraulic circuit 400.

Endcap 538 houses a contact switch 548 having a contact 550 that faces toward piston 536. A wire 545 is coupled to contact switch 548. A plunger 541 is disposed in piston 536. When drawdown of piston assembly 72 is complete, as shown in FIG. 12, piston 536 actuates contact switch 548 by causing plunger 541 to engage contact 550, which causes wire 545 to couple to system ground via contact switch 548 to plunger 541 to piston 536 to endcap 538 which is in communication with system ground (not shown).

It will be understood that the draw down pistons may vary in size such that their volumes vary. The pistons may also be configured to draw down at varying pressures. The embodiment just described includes two draw down piston assemblies, but the formation tester tool may include more or less than two.

The hydraulic circuit 400 used to operate formation probe assemblies 50, 200, equalizer valve 60 and draw down pistons 70, 72 is shown in FIG. 9. A microprocessor-based controller 402 is electrically coupled to all of the controlled elements in the hydraulic circuit 400 illustrated in FIG. 9, although the electrical connections to such elements are conventional and are not illustrated other than schematically. Controller 402 is located in electronics module 20, shown in FIG. 2A, although it could be housed elsewhere in tool 10 or bottom hole assembly 6. Controller 402 detects the control signals transmitted from a master controller 401 housed in the MWD sub 13 of the bottom hole assembly 6 which, in turn, receives instructions transmitted from the surface via mud pulse telemetry, or any of various other conventional means for transmitting signals to downhole tools.

When controller 402 receives a command to initiate formation testing, the drill string has stopped rotating if tool 10 is disposed on a drill sting. As shown in FIG. 9, motor 404 is coupled to pump 406 which draws hydraulic fluid out of hydraulic reservoir 408 through a serviceable filter 410. As will be understood, the pump 406 directs hydraulic fluid into hydraulic circuit 400 that includes formation probe assembly 50, 200 (either can be used interchangeably), equalizer valve 60, draw down pistons 70, 72 and solenoid valves 412, 414, 416, 418, 420, 422. It will be understood that although the description below will reference only formation probe assembly 50, the hydraulic circuit described may be used to operate formation probe assembly 50 or probe assembly 200.

The operation of formation tester 10 is best understood with reference to FIG. 9 in conjunction with FIGS. 6A-6B, 7A-F, 11 and 12. In response to an electrical control signal, controller 402 energizes retract solenoid valve 412 and valve 414, and starts motor 404. Pump 406 then begins to pressurize hydraulic circuit 400 and, more particularly, charges probe retract accumulator 424. The act of charging accumulator 424 also ensures that the formation probe assembly 50 is retracted, the equalizer valve 60 is open and that draw down pistons 70, 72 are in their initial shouldered position as described with reference to FIGS. 11 and 12. When the pressure in system 400 reaches a predetermined value, such as 1800 p.s.i. as sensed by pressure transducer 426a, controller 402 (which continuously monitors pressure in the system) energizes extend solenoid valve 416 which causes formation probe assembly 50 to begin to extend toward the borehole wall 16. Concurrently, check valve 428 and relief valve 429 seal the probe retract accumulator 424 at a pressure charge of between approximately 500 to 1250 p.s.i. Solenoid valve 412 is still energized.

Formation probe assembly 50 extends, as previously described, from the position shown in FIG. 6A to a position before full extension as shown in FIG. 6B (except with snorkel still retracted), where seal pad 180 engages the mud cake 49 on borehole wall 16. At this point, retract solenoid valve 412 is de-energized, thereby allowing snorkel 98 to be extended and scraper 160 to be retracted. With hydraulic pressure continuing to be supplied to the extend side of piston 96 and snorkel 98 for formation probe assembly 50, the snorkel may then penetrate the mud cake and the scraper retracted, as shown in FIG. 6B (and FIGS. 7E-7F for assembly 200). The outward extensions of pistons 96 and snorkel 98 continue until seal pad 180 engages the borehole wall 16, as previously described with regard to formation probe assembly 50. This combined motion continues until the pressure pushing against the extend side of piston 96 and snorkel 98 reaches a pre-determined magnitude, for example 1,200 p.s.i., controlled by relief valve 417, causing seal pad 180 to be squeezed. At this point, a second stage of expansion takes place with snorkel 98 then moving within the cylinders 120 in piston 96 to penetrate the mud cake 49 on the borehole wall 16 and to receive formation fluids or take other measurements.

De-energizing solenoid valve 412 also closes equalizer valve 60, thereby isolating fluid passageway 93 from the annulus. In this manner, valve 412 ensures that valve 60 closes only after the seal pad 140 has entered contact with mud cake 49 which lines borehole wall 16. Passageway 93, now closed to the annulus 15, is in fluid communication with cylinders 512, 542 at the upper ends of cylinders 514, 544 in draw down piston assemblies 70, 72, best shown in FIGS. 11 and 12.

With extend solenoid valve 416 still energized, and the hydraulic circuit 400 at approximately 1,200 p.s.i., probe extend accumulator 430 has been charged and controller 402 energizes solenoid valve 414. Energizing valve 414 closes off the extend section of the hydraulic circuit, thereby maintaining the extend section at approximately 1,200 p.s.i. and allowing drawdown to begin. With valve 414 energized, pressure can be added to the draw down circuit, which generally includes draw down accumulator 432, solenoid valves 418, 420, 422 and draw down piston assemblies 70, 72.

Controller 402 now energizes solenoid valve 420 which permits pressurized fluid to enter portion 504a of cylinder 504 causing draw down piston 70 to retract. When that occurs, plunger 510 moves within cylinder 514 such that the volume of fluid passageway 93 increases by the volume of the area of the plunger 510 times the length of its stroke along cylinder 514. The volume of cylinder 512 is increased by this movement, thereby increasing the volume of fluid in passageway 93. Preferably, these elements are sized such that the volume of fluid passageway 93 is increased by preferably 30 cc maximum as a result of piston 70 being retracted.

If draw down piston 70 is to be stopped due to, for example, the need for only a partial draw down or an unsuccessful partial draw down, controller 402 may energize solenoid valve 418 to pressurize the draw down shutoff valve assembly 74. Pressurizing valve assembly 74 causes draw down piston 70 to cease drawing down formation fluids. Now, valve assembly 74 and draw down piston 70 have been pressured up to approximately 1,800 p.s.i. This ensures that shutoff valve assembly 74 holds draw down piston 70 in its drawn down, or partially drawn down, position such that the drawn formation fluids are retained and not inadvertently expelled.

When it is desired to continue drawing down with draw down piston 70, solenoid valve 418 can be de-energized, thereby turning shutoff valve 74 off. Draw down with draw down piston 70 then commences until the volume of cylinder 514 filled. The draw down of draw down piston 70 may continue to be interrupted using valves 418 and 74. Such interruptions may be necessary to change draw down parameters, such as draw down rate and volume.

Controller 402 may be used to command draw down piston 70 to draw down fluids at differing rates and volumes. For example, draw down piston 70 may be commanded to draw down fluids at 1 cc per second for 10 cc and then wait 5 minutes. If the results of this test are unsatisfactory, a downlink signal may be sent using mud pulse telemetry, or another form of downhole communication, programming controller 402 to command piston 70 to now draw down fluids at 2 cc per second for 20 cc and then wait 10 minutes, for example. The first test may be interrupted, parameters changed and the test may be restarted with the new parameters that have been sent from the surface to the tool. These parameter changes may be made while formation probe assembly 50 is extended.

While draw down piston 70 is stopped, controller 402 may energize solenoid valve 422 which permits pressurized fluid to enter portion 534*a* of cylinder 534 causing draw down piston 72 to retract. When that occurs, plunger 540 moves within cylinder 534 such that the volume of fluid passageway 93 increases by the volume of the area of the plunger 540 times the length of its stroke along cylinder 544. The volume of cylinder 542 is increased by this movement, thereby increasing the volume of fluid in passageway 93. Preferably, these elements are sized such that the volume of fluid passageway 93 is increased by 50 cc as a result of piston 72 being retracted. Preferably, draw down piston 72 does not have the stop and start feature of piston 70, and is able to draw down more fluids at a faster rate. Thus, draw down piston 72 may be configured to draw down fluids at rates of 3.8 or 7.7 cc per second, for example. However, it should be understood that either piston 70, 72 may be different sizes, and piston 72 may also be configured to have the stop and start feature via the shutoff valve assembly. Thus, hydraulic circuit 400 may be configured to operate multiple pistons 70 and/or multiple pistons 72. Also, pistons 70, 72 may be operated in any order.

The ability to control draw down pistons 70, 72 as described above also allows the operator to purge fluids in the draw down piston assemblies and probe flow lines. For example, if a pre-test volume of fluid has been drawn into the probe, it may be purged by actuating the draw down pistons in the opposite directions. This may be useful for cleaning out any accumulated debris in the flow lines and probe assembly.

Maintaining clean flow lines is important to protecting instruments in the testing tool, and to maintaining the integrity of the formation tests by purging old fluids left in the flow lines. Thus, in another embodiment for keeping the flow lines clean, a mechanical filter may be placed in the flow lines, such as anywhere along flow lines 91, 93 in FIGS. 6A, 6B and 9. Alternatively, the flow lines may be purged by opening equalizer valve 60, pumping out fluids present in the flow lines, then closing equalizer valve 60 in preparation of another draw down sequence.

As draw down piston 70 is actuated, 30 cc of formation fluid will thus be drawn through central passageway 127 of snorkel 98 and through screen 100. The movement of draw down piston 70 within its cylinder 504 lowers the pressure in closed passageway 93 to a pressure below the formation pressure, such that formation fluid is drawn through screen 100 and into apertures 166, through snorkel 98, then through stem passageway 108 to passageway 91 that is in fluid communication with passageway 93 and part of the same closed fluid system. In total, fluid chambers 93 (which include the volume of various interconnected fluid passageways, including passageways in formation probe assembly 50, passageways 91, 93, the passageways interconnecting 93 with draw down pistons 70, 72 and draw down shutoff valve 74) preferably has a volume of approximately 63 cc. If draw down piston 72 is also activated, this volume should increase approximately 30 cc, up to approximately 90 cc total. Drilling mud in annulus 15 is not drawn into snorkel 98 because seal pad 180 seals against the mud cake. Snorkel 98 serves as a conduit through which the formation fluid may pass and the pressure of the formation fluid may be measured in passageway 93 while seal pad 180 serves as a seal to prevent annular fluids from entering the snorkel 98 and invalidating the formation pressure measurement.

Referring momentarily to FIG. 6B, formation fluid is drawn first into the central bore 132 of screen 100. It then passes through slots 134 in screen slotted segment 133 such that particles in the fluid are filtered from the flow and are not drawn into passageway 93. The formation fluid then passes between the outer surface of screen 100 and the inner surface of snorkel extension 126 where it next passes through outlet end 135, apertures 166 in scraper 160, scraper tube 150 and into the central passageway 108 of stem 92.

Screen 100 (and screen 290 of assembly 200) may be optimized for particular applications. For example, if prior knowledge of the formation is obtained, then the screen can be tailored to the type of rock or sediment that is present in the formation. One type of adjustable screen is a gravel-packed screen, which may be used instead of or in conjunction with the slotted screen 100. Generally, a gravel-packed screen is two longitudinal, cylindrical screens of different diameters. The screens are disposed concentrically and the annulus is filled with gravel pack sieve, or a known sand size.

Despite the type of formation encountered, the gravel pack may be tailored to have a 10-to-1 ratio of formation sand size to gravel pack size, which is the preferable formation particle size to gravel particle size ratio. With this ratio, it is expected that the gravel pack screen will have the ability to screen formation particles up to $\frac{1}{10}^{th}$ the size of the nominal formation particle diameter size encountered. With this embodiment, the gravel pack sand size can be tailored to the specific intended application.

In yet another embodiment, the screens 100, 290 as they are illustrated in FIGS. 6B, 7F may be optimized by adjusting the size and number of slits required for a particular application. The slits, or slots, are illustrated schematically as internally slotted segment 133 having slots 134 in FIG. 6B, and internally slotted segment 293 having slots 295. The size and number of slits can be tailored to the particular formation expected to be intersected, and the nominal sand particle size of the produced sand. For example, more slits with smaller openings may be used for smaller nominal formation particle size.

In a further embodiment, the above mentioned adjustment of slot size may be accomplished real-time. In the previous embodiment, the slot size is set upon deployment of tool 10 into the borehole. The slot size remains unchanged while tool 10 is deployed. The slot size may be adjusted at the surface of the borehole by replacing screens 100, 290, or by manually adjusting the slot sizes, but may not be adjusted real-time, or while tool 10 is deployed downhole. In the current embodiment, detection of the type of formation actually intersected may be achieved via the various apparatus and methods disclosed herein. If the detected formation value, such as particle size, differs from a predetermined value, the slot size may be adjusted without tripping tool 10 out of the borehole. A command may be given from the surface of the borehole, or from tool 10, and slot size may be adjusted by moving two concentrically disposed slotted cylindrical members relative to each other, for example, or by adjusting shutter mechanisms adjacent the slots.

Referring again to FIG. 9, with seal pad 180 sealed against the borehole wall, check valve 434 maintains the desired pressure acting against piston 96 and snorkel 98 to maintain the proper seal of seal pad 180. Additionally, because probe seal accumulator 430 is fully charged, should tool 10 move during drawdown, additional hydraulic fluid volume may be supplied to piston 96 and snorkel 98 to ensure that seal pad 180 remains tightly sealed against the borehole wall. In addition, should the borehole wall 16 move in the vicinity of seal pad 180, the probe seal accumulator 430 will supply additional hydraulic fluid volume to piston 96 and snorkel 98 to ensure that seal pad 180 remains tightly sealed against the borehole wall 16. Without accumulator 430 in circuit 400, movement of the tool 10 or borehole wall 16, and thus of formation probe assembly 50, could result in a loss of seal at seal pad 180 and a failure of the formation test.

With the drawdown pistons 70, 72 in their fully, or partially, retracted positions and anywhere from one to 90 cc of formation fluid drawn into closed system 93, the pressure will stabilize enabling pressure transducers 426b,c to sense and measure formation fluid pressure. The measured pressure is transmitted to the controller 402 in the electronic section where the information is stored in memory and, alternatively or additionally, is communicated to the master controller 401 in the MWD tool 13 below formation tester 10 where it can be transmitted to the surface via mud pulse telemetry or by any other conventional telemetry means.

When drawdown is completed, pistons 70, 72 actuate their contact switches previously described. When the contact switch 550, for example, is actuated controller 402 responds by shutting down motor 404 and pump 406 for energy conservation. Check valve 436 traps the hydraulic pressure and maintains pistons 70, 72 in their retracted positions. In the event of any leakage of hydraulic fluid that might allow pistons 70, 72 to begin to move toward their original shouldered positions, drawdown accumulator 432 will provide the necessary fluid volume to compensate for any such leakage and thereby maintain sufficient force to retain pistons 70, 72 in their retracted positions.

During this interval, controller 402 continuously monitors the pressure in fluid passageway 93 via pressure transducers 426 b, c. When the measured pressure stabilizes, or after a predetermined time interval, controller 402 de-energizes extend solenoid valve 416. When this occurs, pressure is removed from the close side of equalizer valve 60 and from the extend side of probe piston 96. Equalizer valve 60 will return to its normally open state and probe retract accumulator 424 will cause piston 96 and snorkel 98 to retract, such that seal pad 180 becomes disengaged with the borehole wall. Thereafter, controller 402 again powers motor 404 to drive pump 406 and again energizes solenoid valve 412. This step ensures that piston 96 and snorkel 98 have fully retracted and that the equalizer valve 60 is opened. Given this arrangement, the formation tool has a redundant probe retract mechanism. Active retract force is provided by the pump 406. A passive retract force is supplied by probe retract accumulator 424 that is capable of retracting the probe even in the event that power is lost. It is preferred that accumulator 424 be charged at the surface before being employed downhole to provide pressure to retain the piston and snorkel in housing 12.

It will be understood that the equalizer valve 60 may be opened in a similar manner at other times during probe engagement with the borehole wall. If the probe seal pad is in danger of becoming stuck on the borehole wall, the suction may be broken by opening equalizer valve 60 as described above.

After a predetermined pressure, for example 1800 p.s.i., is sensed by pressure transducer 426a and communicated to controller 402 (indicating that the equalizer valve is open and that the piston and snorkel are fully retracted), controller 402 de-energizes solenoid valves 418, 420, 422 to remove pressure from sides 504a, 534a of drawdown pistons 70, 72, respectively. With solenoid valve 412 remaining energized, positive pressure is applied to sides 504b, 534b of drawdown pistons 70, 72 to ensure that pistons 70, 72 are returned to their original positions. Controller 402 monitors the pressure via pressure transducer 426a and when a predetermined pressure is reached, controller 402 determines that pistons 70, 72 are fully returned and it shuts off motor 404 and pump 406 and de-energizes solenoid valve 412. With all solenoid valves returned to their original positions and with motor 404 off, tool 10 is back in its original condition.

The hydraulic circuit 400, as described and illustrated in FIG. 9, may also act as a regenerative circuit while extending the probe assembly. With both retract valve 412 and extend valve 416 energized or actuated, as described above, and the difference in areas between the smaller area on the retract side of the probe piston, such as piston 96 or piston 240, and the larger area on the extend side of the piston, there is a net effect of extending the probe assembly. As the piston continues to extend with retract valve still open, there is a back flow of hydraulic fluid through retract valve 412 due to the lack of a check valve behind retract valve 412. This relatively unimpeded back flow path leads into the pressurized hydraulic fluid flowing into extend valve 416, adding to the pressure on the extend side of the circuit and increasing the rate at which the probe may extend.

During extension of the probe assembly, using hydraulic circuit 400, it can be seen that the total volume of hydraulic fluid required to be displaced by pump 406, and hence the number of revolutions of motor 404, is reduced compared to a non-regenerative circuit. The regenerative nature of circuit 400 also allows the moveable wiper or scraper, such as scraper 160, to remain extended during extension of the probe assembly, especially as the snorkel assembly is penetrating the mudcake and formation and there is an extra force pushing back on the moveable scraper. As can be seen in FIGS. 6A, 6B and 7A-7F, the area of the extend side of the scraper assembly, for example, the bottom of flange 372 of scraper tube 278 in FIG. 7F, is greater than the area of the retract side, or the upper side of flange 372. Thus, with both valves 412 and 416 actuated, the same hydraulic pressure acts on different areas, causing the wiper element to extend and the pressurized fluid to regenerate on the extend side of the scraper tube 278, as previously described.

Further, as mentioned before, the regeneration of pressure in circuit 400 allows faster extension of the probe assembly. In addition, the regenerated pressure assists with control of equalizer valve actuation.

Figure 10H:
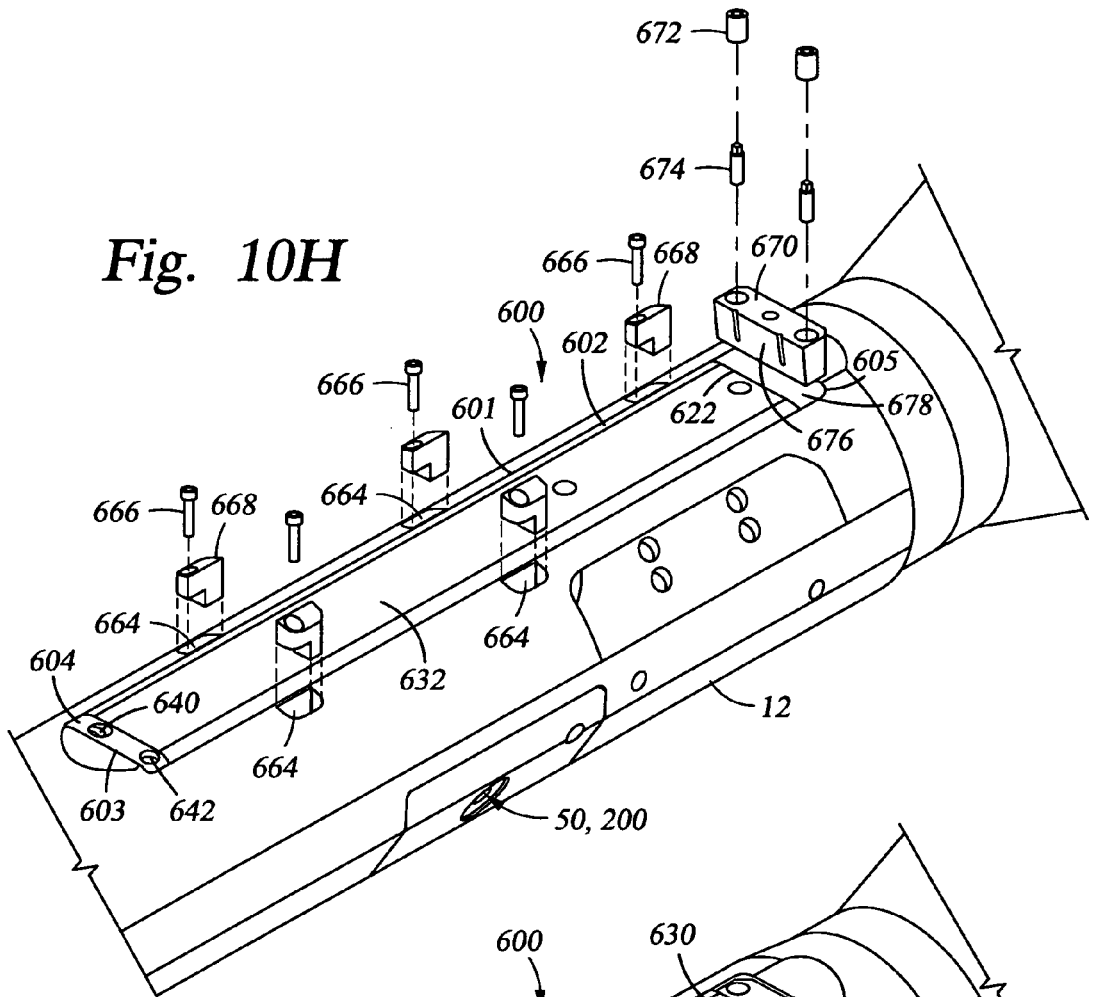
FIGS. 10H-10I are perspective views of the reservoir accumulator assembly and probe collar.
Figure 10I:
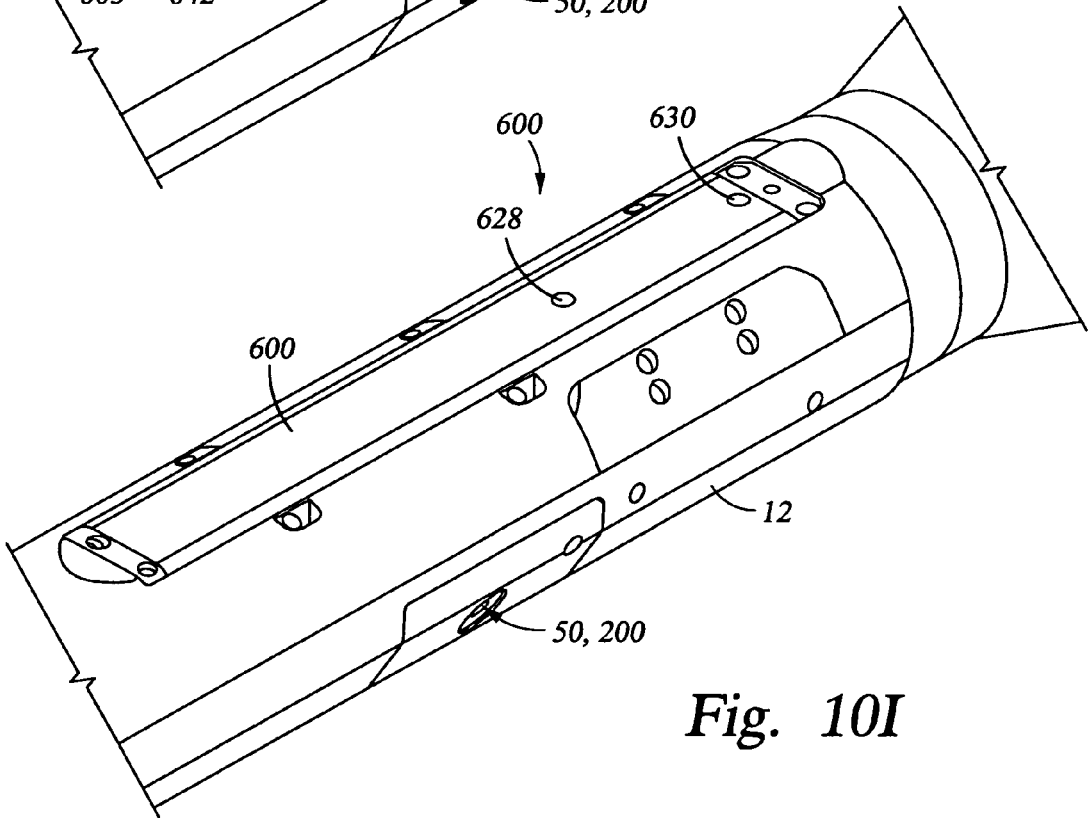

A hydraulic reservoir accumulator assembly 600 is disposed in probe collar 12 as shown in FIG. 10I. Reservoir accumulator assembly 600 maintains a pressure above the annulus or surrounding environment pressure in the complete tool 10 hydraulic system. This condition in the hydraulic system compensates for pressure and temperature changes in the tool. Also, the pressure provided from assembly 600 causes pump 406 (FIG. 9) to begin operating from the annulus pressure, thereby reducing the work load that would be required from starting pump 406 at atmospheric pressure. Thus, accumulator assembly 600 may be used to communicate annulus pressure into the tool's hydraulic system. As will be seen below, assembly 600 is self contained and easily field replaceable.

Assembly 600 generally includes a body 602 having a top surface 632, bottom surface 634 (FIG. 10C) and endcap 604 at end 606, several locking wings 608 and drilling fluid apertures 618, 620 at end 622. Top surface 632 includes additional fluid apertures 628, 630 covered by a screen 639 as illustrated in FIG. 10F. Screen 639 is held in place by retaining ring 637, and prevents large particles in the drilling fluid from entering the cylinders and interfering with the reciprocation of the pistons. Endcap 604 includes a pressure plug 638 for connecting assembly 600 to probe collar 12, which helps to lock assembly 600 into place as illustrated in FIG. 10H. Endcap 604 also includes hydraulic fluid check valves 640, 642 for fluid communication with the tool hydraulic circuit, and for checking fluid into assembly 600 and the tool hydraulic system when assembly 600 is removed from collar 12.

Referring briefly to FIG. 10F, it can be seen that the inside of assembly 600 is split into two cylinders 626, 646. FIG. 10C illustrates cylinder 626 retaining a piston 636 which separates cylinder 626 into hydraulic fluid portion 626*a* and drilling fluid portion 626*b*. Piston 636 is reciprocal between the position shown in FIG. 10C and the position of piston 656 shown in FIG. 10D. Spring 624 is retained in cylinder portion 626*b* between piston 636 and end 622. Spring 624 extends past piston end 636*b* around piston 636 and seats on increased piston diameter portion 633. Increased diameter portion 633 is similar to increased diameter portion 653 of piston 656, illustrated in FIG. 10G. At end 622, aperture 620 allows drilling fluids to enter cylinder portion 626*b* and exert the surrounding annulus pressure on side 636*b* of piston 636. Because spring 624 also exerts a force on side 636*b*, the pressure of hydraulic fluid in cylinder portion 626*a* is greater than the annulus pressure. The pressure of the hydraulic fluid in cylinder portion 626*a* is the annulus pressure plus the pressure added by spring 624. Spring 624 may exert, for example, a pressure of approximately 60-80 p.s.i.

Cylinder 646 of FIG. 10D operates in a similar fashion to cylinder 626. Drilling fluid enters cylinder portion 646*b* through aperture 622, thereby exerting the annulus pressure on side 656*b* of piston 656. Spring 644 then increases the pressure on piston 656, causing the hydraulic fluid in cylinder 646*a*, and therefore the hydraulic fluid in the tool hydraulic system, to be greater than the annulus pressure. Spring 644 is shown in the fully compressed position in FIG. 10D.

Referring now to FIG. 10G, enlarged piston end 656*a* includes seal 659 for sealing the drilling mud from the system hydraulic fluid, and scraper 661 for cleaning the cylinder bore 646 as piston 656 reciprocates. Spring 644 seats on increased diameter portion 653. Piston end 636*a* is similar to piston end 656*a* illustrated in FIG. 10G.

Preferably, pistons 636, 656 reciprocate independently of each other while maintaining the pressure in the hydraulic system of the tool. Also, both pistons communicate with the entire tool hydraulic system.

Referring now to FIG. 10H, accumulator assembly 600 is illustrated placed into position in collar 12, but not locked down. To engage assembly 600 with cavity 601 in collar 12, assembly 600 is disposed above cavity 601 and locking wings 608 (FIG. 10A) are aligned with recesses 664. Recesses 664 are L-shaped (not shown) with the bottom portions of the L extending toward endcap 604 and end 603 of cavity 601. Assembly 600 is lowered into cavity 601 with locking wings 608 sliding down through recesses 664 until assembly 600 seats at the bottom of cavity 601 and top surface 632 is substantially flush with the surface of collar 12. Assembly 600 is then moved toward cavity end 603 such that locking wings 608 move into the extending bottom portions of recesses 664 and pressure plug 638 (FIG. 10A) pressure fits into an aperture (not shown) disposed at end 603 of cavity 601. This forward movement also causes a gap 678 to be formed between cavity end 605 and assembly end 622.

To lock assembly 600 into place, a wedge 670 is placed into gap 678. The angled end 622 (illustrated in FIG. 10C) matingly receives the angled side 676 of wedge 670. The wedging action of these mating surfaces ensures that assembly 600 is moved fully forward in cavity 601. Bolts 674 and nuts 672 lock down wedge 670. Further, L-shaped locking pieces 668 are placed into recesses 664 and bolts 666 are used to lock down wings 608. The final locked position of assembly 600 is illustrated in FIG. 10I. Fluid ports 628, 630 communicate with drilling fluid in annulus 15. Fluid entering cylinder portions 626*b* and 646*b* through apertures 618, 620 is screened by slots in wedge 670 (slots not shown).

Removing accumulator assembly 600 requires a process done in reverse of the process just described. While removing assembly 600, check valves 640, 642 close and maintain oil in the tool hydraulic system. Assembly 600 may then be cleaned and/or replaced. Check valves 640, 642 open again once assembly 600 is locked into position. Hydraulic fluid may then be added to make up for any fluid loss, and preferable fluid is added to the extent that pistons 636, 656 are pushed back to the position illustrated in FIG. 10D.

The uplink and downlink commands used by tool 10 are not limited to mud pulse telemetry. By way of example and not by way of limitation, other telemetry systems may include manual methods, including pump cycles, flow/pressure bands, pipe rotation, or combinations thereof. Other possibilities include electromagnetic (EM), acoustic, and wireline telemetry methods. An advantage to using alternative telemetry methods lies in the fact that mud pulse telemetry (both uplink and downlink) requires pump-on operation but other telemetry systems do not.

The down hole receiver for downlink commands or data from the surface may reside within the formation test tool or within an MWD tool 13 with which it communicates. Likewise, the down hole transmitter for uplink commands or data from down hole may reside within the formation test tool 10 or within an MWD tool 13 with which it communicates. In the preferred embodiment specifically described, the receivers and transmitters are each positioned in MWD tool 13 and the receiver signals are processed, analyzed and sent to a master controller 401 in the MWD tool 13 before being relayed to local controller 402 in formation testing tool 10.

The above discussion is meant to be illustrative of the principles and various embodiments of the present invention. While the preferred embodiment of the invention and its method of use have been shown and described, modifications thereof can be made by one skilled in the art without departing from the spirit and teachings of the invention. The embodiments described herein are exemplary only, and are not limiting. Many variations and modifications of the invention and apparatus and methods disclosed herein are possible and are within the scope of the invention. Accordingly, the scope of protection is not limited by the description set out above, but is only limited by the claims which follow, that scope including all equivalents of the subject matter of the claims.

What is claimed is:

1. A downhole apparatus comprising:
a drill collar having an outer surface for interaction with an earth formation;
an extendable sample device recessed beneath said outer surface in a first position to extend beyond said outer surface to a second position toward a portion of the earth formation to be sampled;
a sampling member coupled to said extendable sample device, said sampling member having a bore and a sampling end to extend to a position beyond said outer surface and said extendable sample device second position toward the portion of the earth formation to be sampled, said bore to receive at least formation fluid from the earth formation; and
an adjustable device disposed adjacent said sampling end to prevent borehole contaminants from entering said sampling member;
wherein said adjustable device comprises at least one of a screen, having a bore, coupled to said sampling end and a seal pad, having an aperture, coupled to said extendable sample device.

2. The apparatus of claim 1 further comprising:
a scraper reciprocally disposed within said sampling member bore to frictionally engage said screen.

3. The apparatus of claim 1 wherein said screen comprises at least one of a plurality of slots and a gravel pack.

4. The apparatus of claim 3 wherein a size of said slots and a diameter of said gravel pack particles are adjustable.

5. The apparatus of claim 1 wherein said seal pad is made from a flexible material and further comprises an internal cavity to receive an adjustable volume of fluid, said adjustable volume of fluid comprising at least one of hydraulic fluid, saline solution and silicone gel.

6. The apparatus of claim 5 wherein said volume of fluid comprises an electro-rheological fluid to receive an electrical field.

7. The apparatus of claim 1 further comprising at least one draw-down cylinder coupled to said extendable sample device to receive at least formation fluid from the earth formation.

8. The apparatus of claim 1 further comprising an equalizer valve coupled to said extendable sample device to receive at least formation fluid from the earth formation.

9. The apparatus of claim 1 wherein said extendable sample device comprises at least one sleeve having an aperture and coupled to said drill collar, each aperture of the at least one sleeve to slidably retain a piston coupled to said sampling member.

10. The apparatus of claim 1 further comprising:
a drill string for drilling a borehole in the earth formation;
a drill bit coupled to a distal end of said drill string; and
wherein said drill collar is coupled to said drill string near said drill bit, said drill collar further comprising a plurality of sensors.

11. The apparatus of claim 10 wherein said drill collar further comprises a stabilizer, and wherein said extendable sample device is mounted in said stabilizer.

12. A downhole apparatus comprising:
a sleeve having a bore;
a first piston having a bore, said first piston being slidingly retained within said sleeve bore between a retracted position and an extended position;
a second piston having a bore, said second piston being slidingly retained within said first piston bore between a retracted position and an extended position; and
a snorkel having a bore, said snorkel being slidingly retained within said second piston bore between a retracted position and an extended position, wherein a portion of said snorkel extends beyond said second piston bore when said snorkel is in said snorkel extended position.

13. The apparatus of claim 12 wherein said snorkel further comprises a screen having a bore.

14. The apparatus of claim 13 further comprising:
a scraper reciprocally disposed within said snorkel bore to frictionally engage said screen.

15. The apparatus of claim 12 further comprising a seal pad having an aperture, said seal pad coupled to said second piston, said seal pad to prevent borehole contaminants from entering said snorkel.

16. The apparatus of claim 15 wherein said seal pad is made from a flexible material and further comprises an internal cavity to receive an adjustable volume of fluid, said adjustable volume of fluid comprising at least one of hydraulic fluid, saline solution and silicone gel.

17. The apparatus of claim 16 wherein said volume of fluid comprises an electro-rheological fluid to receive an electrical field.

18. The apparatus of claim 12 further comprising at least one draw-down cylinder communicating with said snorkel to receive at least formation fluid from an earth formation.

19. The apparatus of claim 12 further comprising an equalizer valve communicating with said snorkel to receive at least formation fluid from an earth formation.

20. A method of sampling a formation comprising:
extending from within a drill collar a first piston radially outward;
extending a snorkel coupled to the first piston from the first piston, the snorkel to contact a borehole wall in an earth formation;
removing contaminants from the snorkel;
sealing a volume surrounding the snorkel to prevent contaminants from re-entering the snorkel; and
measuring a property of the formation;
wherein the removing or the sealing is adjustable.

21. The method of claim 20 further comprising:
extending a second piston from within the first piston; and
further extending the snorkel from within the second piston.

22. The method of claim 20 wherein removing contaminants from the snorkel comprises slidably engaging a scraper within the snorkel to remove the contaminants.

23. The method of claim 20 wherein sealing a volume surrounding the snorkel comprises moving a seal pad coupled to any one of the first piston and the snorkel to form a seal with the borehole wall.

24. The method of claim 23 wherein forming a seal with the borehole wall comprises filling a cavity in the seal pad with at least one of hydraulic fluid, saline solution, silicone gel, and an electro-rheological fluid.

25. The method of claim 20 further comprising filtering contaminants adjacent the snorkel.

26. The method of claim 25 wherein filtering contaminants adjacent the snorkel further comprises:
flowing the contaminants over at least one of a plurality of slots in a screen and a gravel pack; and
adjusting at least one of a size of the slots and a diameter of the gravel particles if the formation property differs from a predetermined value.

* * * * *

UNITED STATES PATENT AND TRADEMARK OFFICE
CERTIFICATE OF CORRECTION

PATENT NO. : 7,603,897 B2
APPLICATION NO. : 11/133643
DATED : October 20, 2009
INVENTOR(S) : Gilbert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this

Fifth Day of October, 2010

David J. Kappos
*Director of the United States Patent and Trademark Office*